(12) United States Patent
Cardin et al.

(10) Patent No.: US 8,440,664 B2
(45) Date of Patent: May 14, 2013

(54) HETEROARYLS AND USES THEREOF

(75) Inventors: David P. Cardin, Wilmington, MA (US); Jeffrey Gaulin, Rockingham, NH (US); Paul Greenspan, Acton, MA (US); Christelle C. Renou, Stoneham, MA (US); Stepan Vyskocil, Arlington, MA (US); Tianlin Xu, Shrewsbury, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/449,341

(22) Filed: Apr. 18, 2012

(65) Prior Publication Data

US 2012/0202812 A1 Aug. 9, 2012

Related U.S. Application Data

(63) Continuation of application No. 12/456,455, filed on Jun. 17, 2009, now Pat. No. 8,183,240.

(60) Provisional application No. 61/132,484, filed on Jun. 19, 2008.

(51) Int. Cl.
*A61K 31/535* (2006.01)

(52) U.S. Cl.
USPC .................................................. 514/235.8

(58) Field of Classification Search ................. 514/235.8
See application file for complete search history.

(56) References Cited

U.S. PATENT DOCUMENTS

2006/0041006 A1  2/2006  Ibrahim et al.

FOREIGN PATENT DOCUMENTS

| DE | 275870 A1 | 7/1990 |
|---|---|---|
| WO | WO 2006/078287 A2 | 7/2006 |
| WO | WO 2006/114313 A1 | 11/2006 |
| WO | WO 2007/129044 A1 | 11/2007 |
| WO | WO 2007/129161 A2 | 11/2007 |
| WO | WO 2008/023159 A1 | 2/2008 |
| WO | WO 2009/042607 A1 | 4/2009 |
| WO | WO 2009/094224 A1 | 7/2009 |

OTHER PUBLICATIONS

International Search Report and Written Opinion dated Jun. 10, 2009 from International Application No. PCT/US2009/000513, which relates to U.S. Appl. No. 12/321,871.

International Search Report and Written Opinion dated Sep. 23, 2009 from International Application No. PCT/US2009/003607, which relates to U.S. Appl. No. 12/321,871.
"2-Thiophenecarboxylic acid, 3-(4-chlorophenyl)-4-cyano-5-(4-morpholinyl)-(CA Index Name)," CAS Registry No. 883097-33-4, entered May 5, 2006.
"2-Thiophenecarboxylic acid, 3-(4-chlorophenyl)-4-cyano-5-(4-morpholinyl)-, methyl ester (CA Index Name)," CAS Registry No. 882283-38-7, entered Apr. 30, 2006.
Pinto, Ivan L. et al., "The Synthesis of 5-alkoxy and 5-amino Substituted Thiophenes," *Tetrahedron Letters*, vol. 41, No. 10, (2000), pp. 1597-1600.
Hirai, Kentaro et al., "Heterocyclic Cation Systems. 14. Synthesis of Thieno[3,2-e][1,4]diazepine, Thiazolo[4,5-e][1,4]diazepine, and s-Triazolo[3,4-c]thiazolo[4,5-e][1,4]diazepine Derivatives," *Journal of Organic Chemistry*, vol. 45, (1980), pp. 253-260.
Datta, A. et al., "A Novel Route to Methyl 3-3(3,4-Disubstituted 5-alkylthio/amino-2-thienyl)propenoates," *Synthesis*, vol. 7, (1988), pp. 556-567.
Raap, R., "Some Synthesis With Dimethyl Monothionemalonate," *Canadian Journal of Chemistry*, vol. 46, No. 13, (1968), pp. 2255-2261.
Hirai, Kentaro et al., "Novel Synthesis of Thiophene Derivatives from 1,3-Oxathiol-2-ylideneimmonium Salt," *Chemical & Pharmaceutical Bulletin*, vol. 19, No. 10, (1971), pp. 2194-2197.
"Morpholine, 4-[5-(4,5-diphenyl-1H-imidazol-2-yl)-2-thienyl]-," *Ryan Scientific Screening Library*, Publication Date: Jan. 25, 2008, CAS Registry No. 851954-74-0.
Heyde, Cornelia et al., "A Simple Route to *N-N*-Dialkyl Derivatives of 2-Amino-5-thiophenecarboxylates," *European Journal of Organic Chemistry*, vol. 19, (2000), pp. 3273-3278.
Rehwald, Matthias et al.., "New Syntheses of 2,4-Diaminothiophenes—Use of (1,3-Oxathiol-2-Ylidene)Malononitrile," *Heterocyles*, vol. 45, No. 3, (1997), pp. 493-500.
Database CHEMCATS, Chemical Abstracts Service, Columbus, Ohio, US, XP002545555, order No. T5337328.

*Primary Examiner* — Rebecca Anderson
(74) *Attorney, Agent, or Firm* — Choate, Hall & Stewart LLP; Andrea L. C. Robidoux; Dwight D. Kim

(57) ABSTRACT

This invention provides compounds of formula I:

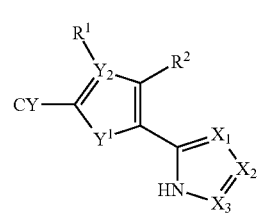

wherein $R^1$, $R^2$, CY, $Y_1$, $Y_2$, $X_1$, $X_2$, and $X_3$ are as described in the specification. The compounds are inhibitors of PI3K and are thus useful for treating proliferative, inflammatory, or cardiovascular disorders.

5 Claims, No Drawings

HETEROARYLS AND USES THEREOF

The present application is a continuation of U.S. patent application Ser. No. 12/456,455, filed Jun. 17, 2009, now U.S. Pat. No. 8,183,240, which claims the benefit of U.S. Provisional Application Ser. No. 61/132,484, filed Jun. 19, 2008 (abandoned). The entire contents of each of the above-referenced patent applications are incorporated herein by this reference.

BACKGROUND OF THE INVENTION

Phosphatidylinositol 3-kinase (PI3K) is a family of lipid kinases that phosphorylate phosphatidylinositol at the 3' position of the inositol ring. PI3K is comprised of several classes of genes, including Class IA, IB, II and III and some of these classes contain several isoforms (reviewed in Engelman et al., Nature Review Genetics 7:606-619 (2006)). Adding to the complexity of this family is the fact that PI3Ks function as heterodimers, comprising a catalytic domain and a regulatory domain. The PI3K family is structurally related to a larger group of lipid and serine/threonine protein kinases known as the phosphatidylinositol 3-kinase like kinases (PIKKs), which also includes DNA-PK, ATM, ATR, mTOR, TRRAP and SMG1.

PI3K is activated downstream of various mitogenic signals mediated through receptor tyrosine kinases, and subsequently stimulates a variety of biological outcomes; including increased cell survival, cell cycle progression, cell growth, cell metabolism, cell migration and angiogenesis (reviewed in Cantley, Science 296:1655-57 (2002); Hennessy et al., Nature Reviews Drug Discovery 4:988-1004 (2005); Engelman et al., Nature Review Genetics 7:606-619 (2006)). Thus, PI3K hyper-activation is associated with a number of hyper-proliferative, inflammatory, or cardiovascular disorders; including cancer, inflammation, and cardiovascular disease.

There are a number of genetic aberrations that lead to constitutive PI3K signaling; including activating mutations in PI3K itself (Hennessy et al., Nature Reviews Drug Discovery, 4:988-1004 (2005); reviewed in Bader et al., Nature Reviews Cancer 5:921-9 (2005)); RAS (reviewed in Downward Nature Reviews Cancer 3:11-22 (2003)) and upstream receptor tyrosine kinases (reviewed in Zwick et al., Trends in Molecular Medicine 8:17-23 (2002)) as well as inactivating mutations in the tumor suppressor PTEN (reviewed in Cully et al., Nature Reviews Cancer 6:184-92 (2006)). Mutations in each of these gene classes have proven to be oncogenic and are commonly found in a variety of cancers.

The molecules defined within this invention inhibit the activity of PI3K, and therefore may be useful for the treatment of proliferative, inflammatory, or cardiovascular disorders. Cases where PI3K pathway mutations have been linked to proliferative disorders where the molecules defined within this invention may have a therapeutic benefit include benign and malignant tumors and cancers from diverse lineage, including but not limited to those derived from colon (Samuels et al., Science 304:554 (2004); reviewed in Karakas et al., British Journal of Cancer 94: 455-59 (2006)), liver (reviewed in Karakas et al., British Journal of Cancer 94: 455-59 (2006)), intestine (reviewed in Hennessy et al., Nature Reviews Drug Discovery 4:988-1004 (2005)), stomach (Samuels et al., Science 304:554 (2004); reviewed in Karakas et al., British Journal of Cancer 94: 455-59 (2006)), esophagus (Phillips et al., International Journal of Cancer 118:2644-6 (2006)); pancreas (reviewed in Downward Nature Reviews Cancer 3:11-22 (2003)); skin (reviewed in Hennessy et al., Nature Reviews Drug Discovery 4:988-1004 (2005)), prostate (reviewed in Hennessy et al., Nature Reviews Drug Discovery 4:988-1004 (2005)), lung (Samuels et al., Science 304:554 (2004); reviewed in Karakas et al., British Journal of Cancer 94: 455-59 (2006)), breast (Samuels et al., Science 304:554 (2004); Isakoff et al., Can Res 65:10992-1000 (2005); reviewed in Karakas et al., British Journal of Cancer 94: 455-59 (2006)), endometrium (Oda et al., Can Res 65:10669-73 (2005); reviewed in Hennessy et al., Nature Reviews Drug Discovery 4:988-1004 (2005)), cervix (reviewed in Hennessy et al., Nature Reviews Drug Discovery 4:988-1004 (2005)); ovary (Shayesteh et al., Nature Genetics 21:99-102 (1999); reviewed in Karakas et al., British Journal of Cancer 94: 455-59 (2006)), testes (Moul et al., Genes Chromosomes Cancer 5:109-18 (1992); Di Vizio et al., Oncogene 24:1882-94 (2005)), hematological cells (reviewed in Karakas et al., British Journal of Cancer 94: 455-59 (2006); Hennessy et al., Nature Reviews Drug Discovery 4:988-1004 (2005)), pancreas (reviewed in Downward Nature Reviews Cancer 3:11-22 (2003)), thyroid (reviewed in Downward Nature Reviews Cancer 3:11-22 (2003); reviewed in Hennessy et al., Nature Reviews Drug Discovery 4:988-1004 (2005)); brain (Samuels et al., Science 304:554 (2004); reviewed in Karakas et al., British Journal of Cancer 94: 455-59 (2006)), bladder (Lopez-Knowles et al., Cancer Research 66:7401-7404 (2006); Hennessy et al., Nature Reviews Drug Discovery 4:988-1004 (2005)); kidney (reviewed in Downward Nature Reviews Cancer 3:11-22 (2003)) and Head and Neck (reviewed in Engelman et al., Nature Reviews Genetics 7:606-619 (2006)).

Other classes of disorders with aberrant PI3K pathway signaling where the molecules defined within this invention may have a therapeutic benefit include inflammatory and cardiovascular diseases, including but not limited to allergies/anaphylaxis (reviewed in Rommel et al., Nature Reviews Immunology 7:191-201 (2007)), acute and chronic inflammation (reviewed in Ruckle et al., Nature Reviews Drug Discovery 5:903-12 (2006); reviewed in Rommel et al., Nature Reviews Immunology 7:191-201 (2007)), rheumatoid arthritis (reviewed in Rommel et al., Nature Reviews Immunology 7:191-201 (2007)); autoimmunity disorders (reviewed in Ruckle et al., Nature Reviews Drug Discovery 5:903-12 (2006)), thrombosis (Jackson et al., Nature Medicine 11:507-14 (2005); reviewed in Ruckle et al., Nature Reviews Drug Discovery 5:903-12 (2006)), hypertension (reviewed in Ruckle et al., Nature Reviews Drug Discovery 5:903-12 (2006)), cardiac hypertrophy (reviewed in Proud et al., Cardiovascular Research 63:403-13 (2004)), and heart failure (reviewed in Mocanu et al., British Journal of Pharmacology 150:833-8 (2007)).

Clearly, it would be beneficial to provide novel PI3K inhibitors that possess good therapeutic properties, especially for the treatment of proliferative, inflammatory, or cardiovascular disorders.

DETAILED DESCRIPTION OF THE INVENTION

1. General Description of Compounds of the Invention:

This invention provides compounds that are inhibitors of PI3K, and accordingly are useful for the treatment of proliferative, inflammatory, or cardiovascular disorders. The compounds of this invention are represented by formula I:

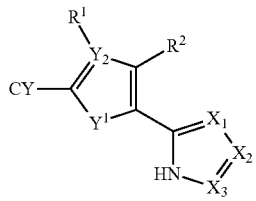

or a pharmaceutically acceptable salt thereof, wherein:
when $Y_2$ is C, $R^1$ is H, —CN, halogen, —Z—$R^3$, $C_{1-6}$ aliphatic, or 3-10-membered cycloaliphatic, wherein:
Z is selected from an optionally substituted $C_{1-3}$ alkylene chain, —O—, —N($R^{1a}$)—, —S—, —S(O)—, —S(O)$_2$—, —C(O)—, —CO$_2$—, —C(O)N$R^{1a}$—, —N($R^{1a}$)C(O)—, —N($R^{1a}$)CO$_2$—, —S(O)$_2$N$R^{1a}$—, —N($R^{1a}$)S(O)$_2$—, —OC(O)N($R^{1a}$)—, —N($R^{1a}$)C(O)N$R^{1a}$—, —N($R^{1a}$)S(O)$_2$N($R^{1a}$)—, or —OC(O)—;
$R^{1a}$ is hydrogen or an optionally substituted $C_{1-4}$ aliphatic, and
$R^3$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
$R^2$ is H, halogen, —W—$R^5$, or —$R^5$, wherein:
W is selected from an optionally substituted $C_{1-3}$ alkylene chain, —O—, —N($R^{2a}$)—, —S—, —S(O)—, —S(O)$_2$—, —C(O)—, —CO$_2$—, —C(O)N$R^{2a}$—, —N($R^{2a}$)C(O)—, —N($R^{2a}$)CO$_2$—, —S(O)$_2$N$R^{2a}$—, —N($R^{2a}$)S(O)$_2$—, —OC(O)N($R^{2a}$)—, —N($R^{2a}$)C(O)N$R^{2a}$—, —N($R^{2a}$)S(O)$_2$N($R^{2a}$)—, or —OC(O)—.
$R^{2a}$ is hydrogen or an optionally substituted $C_{1-4}$ aliphatic, and
$R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
$X_1$, $X_2$, and $X_3$ are each independently N or C$R^6$, wherein each occurrence of $R^6$ is independently hydrogen, —CN, halogen, —V—$R^7$, $C_{1-6}$ aliphatic, or 3-10-membered cycloaliphatic, wherein:
V is selected from an optionally substituted $C_{1-3}$ alkylene chain, —O—, —N($R^{6a}$)—, —S—, —S(O)—, —S(O)$_2$—, —C(O)—, —CO$_2$—, —C(O)N$R^{6a}$—, —N($R^{6a}$)C(O)—, —N($R^{6a}$)CO$_2$—, —S(O)$_2$N$R^{6a}$—, —N($R^{6a}$)S(O)$_2$—, —OC(O)N($R^{6a}$)—, —N($R^{6a}$)C(O)N$R^{6a}$—, —N($R^{6a}$)S(O)$_2$N($R^{6a}$)—, or —OC(O)—.
$R^{6a}$ is hydrogen or an optionally substituted $C_{1-4}$ aliphatic, and
$R^7$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$Y_1$ is S, O, N$R^8$, wherein $R^8$ is hydrogen or an optionally substituted $C_{1-4}$ aliphatic;
$Y_2$ is C, N
CY is

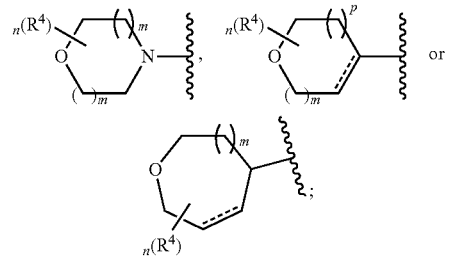

wherein each occurrence of $R^4$ is independently —$R^{4a}$ or -$T_1$-$R^{4d}$, wherein:
each occurrence of $R^{4a}$, as valency and stability permit, is independently fluorine, =O, =S, —CN, —NO$_2$, —$R^{4c}$, —N($R^{4b}$)$_2$, —O$R^{4b}$, —S$R^{4c}$, —S(O)$_2$$R^{4c}$, —C(O)$R^{4b}$, —C(O)O$R^{4b}$, —C(O)N($R^{4b}$)$_2$, —S(O)$_2$N ($R^{4b}$)$_2$, —OC(O)N($R^{4b}$)$_2$, —N($R^{4e}$)C(O)$R^{4b}$, —N($R^{4e}$)SO$_2$$R^{4c}$, —N($R^{4e}$)C(O)O$R^{4b}$, —N($R^{4e}$)C(O)N($R^{4b}$)$_2$, or —N($R^{4e}$)SO$_2$N($R^{4b}$)$_2$, or two occurrences of $R^{4b}$, taken together with a nitrogen atom to which they are bound, form an optionally substituted 4-7-membered heterocyclyl ring having 0-1 additional heteroatoms selected from nitrogen, oxygen, or sulfur;
each occurrence of $R^{4b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{4c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{4d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^{4e}$ is independently hydrogen or an optionally substituted $C_{1-6}$ aliphatic group; and
$T_1$ is an optionally substituted $C_1$-$C_6$ alkylene chain wherein the alkylene chain optionally is interrupted by —N($R^{4a}$)—, —O—, —S—, —S(O)—, —S(O)$_2$—, —C(O)—, —C(O)O—, —C(O)N($R^{4a}$)—, —S(O)$_2$N ($R^{4a}$)—, —OC(O)N($R^{4a}$)—, —N($R^{4a}$)C(O)—, —N($R^{4a}$)SO$_2$—, —N($R^{4a}$)C(O)O—, —N$R^{4a}$C(O)N ($R^{4a}$)—, —N($R^{4a}$)S(O)$_2$N($R^{4a}$)—, —OC(O)—, or —C(O)N($R^{4a}$)—O— or wherein $T_1$ or a portion thereof optionally forms part of an optionally substituted 3-7 membered cycloaliphatic or heterocyclyl ring;

n is 0-6;

m is 1 or 2;

p is 0, 1, or 2;

≈≈≈ represents a single or double bond; and provided that the compound of formula I is other than Morpholine, 4-[5-(4,5-diphenyl-1H-imidazol-2-yl)-2-thienyl]-.

2. Compounds and Definitions:

Compounds of this invention include those described generally for formula I above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, 4H-quinoxalinyl, carbazolyl, acridinyl, phenazinyl, phenothiazinyl, phenoxazinyl, tetrahydroquinolinyl, tetrahydroisoquinolinyl, and pyrido[2,3-b]-1, 4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl.

A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroaralkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —$NO_2$, —CN, —$R^+$, —$C(R^+)=C(R^+)_2$, —C≡C—$R^+$, —$OR^+$, —$SR^\circ$, —$S(O)R^\circ$, —$SO_2R^\circ$, —$SO_3R^+$, —$SO_2N(R^+)_2$, —$N(R^+)_2$, —$NR^+C(O)R^+$, —$NR^+C(S)R^+$, —$NR^+C(O)N(R^+)_2$, —$NR^+C(S)N(R^+)_2$, —$N(R^+)C(=NR^+)$—$N(R^+)_2$, —$N(R^+)C(=NR^+)$—$R^\circ$, —$NR^+CO_2R^+$, —$NR^+SO_2R^\circ$, —$NR^+SO_2N(R^+)_2$, —O—$C(O)R^+$, —O—$CO_2R^+$, —$OC(O)N(R^+)_2$, —$C(O)R^+$, —$C(S)R^\circ$, —$CO_2R^+$, —C(O)—$C(O)R^+$, —$C(O)N(R^+)_2$, —$C(S)N(R^+)_2$, —C(O)N($R^+$)—$OR^+$, —$C(O)N(R^+)C(=NR^+)$—$N(R^+)_2$, —$N(R^+)C(=NR^+)$—$N(R^+)$—$C(O)R^+$, —$C(=NR^+)$—$N(R^+)_2$, —$C(=NR^+)$—$OR^+$, —$N(R^+)$—$N(R^+)_2$, —$C(=NR^+)$—$N(R^+)$—$OR^+$, —$C(R^\circ)=N$—$OR^+$, —$P(O)(R^+)_2$, —$P(O)(OR^+)_2$, —O—$P(O)$—$OR^+$, and —$P(O)(NR^+)$—$N(R^+)_2$, wherein $R^+$, independently, is hydrogen or an optionally substituted aliphatic, aryl, heteroaryl, cycloaliphatic, or heterocyclyl group, or two independent occurrences of $R^+$ are taken together with their intervening atom(s) to form an optionally substituted 5-7-membered aryl, heteroaryl, cycloaliphatic, or heterocyclyl ring. Each $R^\circ$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R°=N—NHSO$_2$R° or =N—R* where R° is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR$^+$

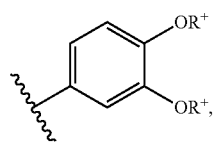

these two occurrences of R$^+$ are taken together with the oxygen atoms to which they are bound to form a fused 6-membered oxygen containing ring:

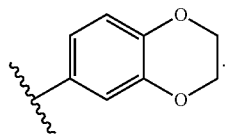 [SMILES: *c1ccc2c(c1)OCCO2]

It will be appreciated that a variety of other rings (e.g., spiro and bridged rings) can be formed when two independent occurrences of R$^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography;selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s)

and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds:

In certain embodiments, for compounds of general formula I, one or more substituents are selected from:

(a) $Y_1$ is S;

(b) $Y_2$ is C (c) $R^1$ is CN or H;

(d) $R^2$ is an optionally substituted 6-10-membered aryl, or 5-10-membered heteroaryl having 1-5 heteroatoms independently selected from nitrogen, oxygen, or sulfur;

(e) n is 0-2; or (f) $R^4$ is —$R^{4a}$.

In some embodiments, a compound of formula I is represented by:

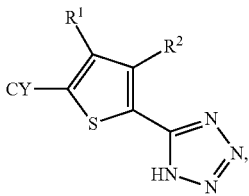

I-A

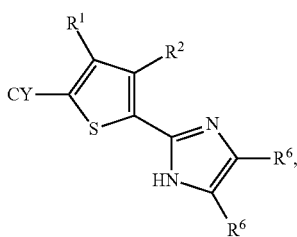

I-B

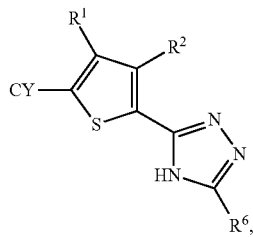

I-C

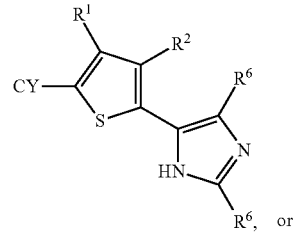

I-D

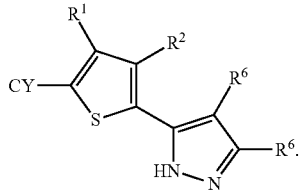

I-E

In yet other embodiments, $R^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of $R^9$, wherein $R^9$ is —$R^{9a}$, -$T_2$-$R^{9d}$, or —$V_2$-$T_2$-$R^{9d}$, and:

each occurrence of $R^{9a}$ is independently halogen, —CN, —$NO_2$, —$R^{9c}$, —$N(R^{9b})_2$, —$OR^{9b}$, —$SR^{9c}$, —$S(O)_2R^{9c}$, —$C(O)R^{9b}$, —$C(O)OR^{9b}$, —$C(O)N(R^{9b})_2$, —$S(O)_2N(R^{9b})_2$, —$OC(O)N(R^{9b})_2$, —$N(R^{9e})C(O)R^{9b}$, —$N(R^{9e})SO_2R^{9c}$, —$N(R^{9e})C(O)OR^{9b}$, —$N(R^{9e})C(O)N(R^{9b})_2$, or —$N(R^{9e})SO_2N(R^{9b})_2$, or two occurrences of $R^{9b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{9b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9e}$ is independently hydrogen or an optionally substituted $C_{1-6}$ aliphatic group;

each occurrence of $V_2$ is independently —$N(R^{9e})$—, —O—, —S—, —S(O)—, —$S(O)_2$—, —C(O)—, —C(O)O—, —$C(O)N(R^{9e})$—, —$S(O)_2N(R^{9e})$—, —$OC(O)N(R^{9e})$—, —$N(R^{9e})C(O)$—, —$N(R^{9e})SO_2$—, —N(R$^{9e}$)C(O)O—, —NR$^{9e}$C(O)N(R$^{9e}$)—, —N(R$^{9e}$)SO$_2$N(R$^{9e}$)—, —OC(O)—, or —C(O)N(R$^{9e}$)—O—; and T$_2$ is an optionally substituted C$_1$-C$_6$ alkylene chain wherein the alkylene chain optionally is interrupted by —N(R$^{7a}$)—, —O—, —S—, —S(O)—, —S(O)$_2$—, —C(O)—, —C(O)O—, —C(O)N(R$^{7a}$)—, —S(O)$_2$N(R$^{7a}$)—, —OC(O)N(R$^{7a}$)—, —N(R$^{7a}$)C(O)—, —N(R$^{7a}$)SO$_2$—, —N(R$^{7a}$)C(O)O—, —NR$^{7a}$C(O)N(R$^{7a}$)—, —N(R$^{7a}$)S(O)$_2$N(R$^{7a}$)—, —OC(O)—, or —C(O)N(R$^{7a}$)—O— or wherein T$_3$ or a portion thereof optionally forms part of an optionally substituted 3-7 membered cycloaliphatic or heterocyclyl ring.

In still other embodiments, Y$_1$ is S, Y$_2$ is C and the compound is represented by formula II:

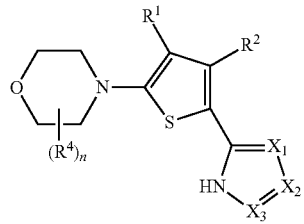

II wherein R$^1$ is CN or H.

In yet other embodiments, R$^2$ is an optionally substituted 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

n is 0-2; and

R$^4$ is —R$^{4a}$.

In still other embodiments, a compound of formula I is represented by:

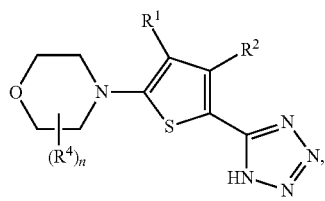

II-A

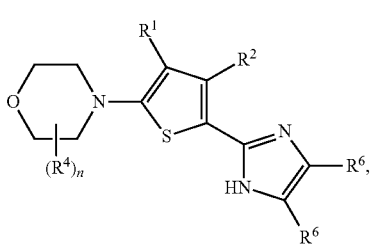

II-B

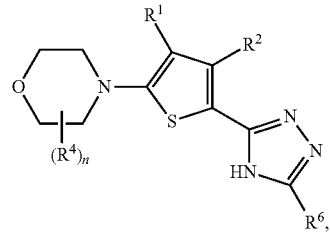

II-C

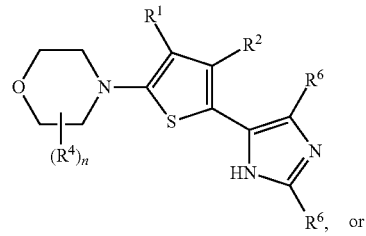

II-D

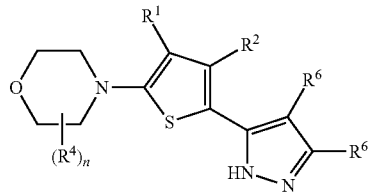

II-E

In still other embodiments, for compounds described directly above, R$^2$ is a 3-10-membered cycloaliphatic, 4-10-membered heterocyclyl having 1-5 heteroatoms independently selected from nitrogen, oxygen, or sulfur 6-10-membered aryl, or 5-10-membered heteroaryl having 1-5 heteroatoms independently selected from nitrogen, oxygen, or sulfur, optionally substituted with 1-4 independent occurrences of R$^9$, wherein R$^9$ is —R$^{9a}$, -T$_2$-R$^{9d}$, or —V$_2$-T$_2$-R$^{9d}$, and:

each occurrence of R$^{9a}$ is independently halogen, —CN, —NO$_2$, —R$^{9c}$, —N(R$^{9b}$)$_2$, —OR$^{9b}$, —SR$^{9c}$, —S(O)$_2$R$^{9c}$, —C(O)R$^{9b}$, —C(O)OR$^{9b}$, —C(O)N(R$^{9b}$)$_2$, —S(O)$_2$ N(R$^{9b}$)$_2$, —OC(O)N(R$^{9b}$)$_2$, —N(R$^{9e}$)C(O) R$^{9b}$, —N(R$^{9e}$)SO$_2$R$^{9c}$, —N(R$^{9e}$)C(O)OR$^{9b}$, —N(R$^{9e}$)C(O)N(R$^{9b}$)$_2$, or —N(R$^{9e}$)SO$_2$N(R$^{9b}$)$_2$, or two occurrences of R$^{9b}$, taken together with a nitrogen atom to which they are bound, form an optionally substituted 4-7-membered heterocyclyl ring having 0-1 additional heteroatoms selected from nitrogen, oxygen, or sulfur;

each occurrence of R$^{9b}$ is independently hydrogen or an optionally substituted group selected from C$_1$-C$_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{9c}$ is independently an optionally substituted group selected from C$_1$-C$_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of R$^{9d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{9e}$ is independently hydrogen or an optionally substituted $C_{1-6}$ aliphatic group;

each occurrence of $V_2$ is independently —N($R^{9e}$)—, —O—, —S—, —S(O)—, —S(O)$_2$—, —C(O)—, —C(O)O—, —C(O)N($R^{9e}$)—, —S(O)$_2$N($R^{9e}$)—, —OC(O)N($R^{9e}$)—, —N($R^{9e}$)C(O)—, —N($R^{9e}$)SO$_2$—, —N($R^{9e}$)C(O)O—, —N$R^{9e}$C(O)N($R^{9e}$)—, —N($R^{9e}$)SO$_2$N($R^{9e}$)—, —OC(O)—, or —C(O)N($R^{9e}$)—O—; and $T_2$ is an optionally substituted $C_1$-$C_6$ alkylene chain wherein the alkylene chain optionally is interrupted by —N($R^{7a}$)—, —O—, —S—, —S(O)—, —S(O)$_2$—, —C(O)—, —C(O)O—, —C(O)N($R^{7a}$)—, —S(O)$_2$N($R^{7a}$)—, —OC(O)N($R^{7a}$)—, —N($R^{7a}$)C(O)—, —N($R^{7a}$)SO$_2$—, —N($R^{7a}$)C(O)O—, —N$R^{7a}$C(O)N($R^{7a}$)—, —N($R^{7a}$)S(O)$_2$N($R^{7a}$)—, —OC(O)—, or —C(O)N($R^{7a}$)—O— or wherein $T_3$ or a portion thereof optionally forms part of an optionally substituted 3-7 membered cycloaliphatic or heterocyclyl ring.

In yet other embodiments, $R^2$ is a phenyl group substituted with 1-3 independent occurrences of halogen, —CN, —NO$_2$, —$R^{9c}$, —N($R^{9b}$)$_2$, —O$R^{9b}$, —S$R^{9c}$, —S(O)$_2R^{9c}$, —C(O)$R^{9b}$, —C(O)O$R^{9b}$, —C(O)N($R^{9b}$)$_2$, —S(O)$_2$N($R^{9b}$)$_2$, —OC(O)N($R^{9b}$)$_2$, —N($R^{9e}$)C(O)$R^{9b}$, —N($R^{9e}$)SO$_2R^{9c}$, —N($R^{9e}$)C(O)O$R^{9b}$, —N($R^{9e}$)C(O)N($R^{9b}$)$_2$, or —N($R^{9e}$)SO$_2$N($R^{9b}$)$_2$;

$R^3$ is hydrogen, $C_{1-4}$alkyl, or $C_{1-4}$fluoroalkyl; and n is 0.

In still other embodiments, $R^2$ is a phenyl group substituted with 1-3 independent occurrences of halo, $C_{1-3}$ alkyl, CN, $C_{1-3}$haloalkyl, —O$C_{1-3}$ alkyl, —O$C_{1-3}$ haloalkyl, —NHC(O)$C_{1-3}$ alkyl, —NHC(O)NHC$_{1-3}$ alkyl, NHS(O)$_2C_{1-3}$ alkyl, or —COH.

Table 1 below depicts certain exemplary compounds of formula I:

TABLE 1

| Exemplary Compounds of formula I: |
| --- |

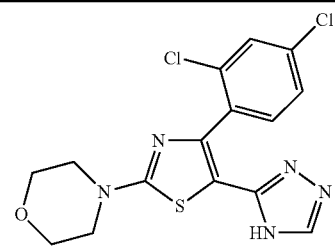

1
4-[4-(2,4-dichlorophenyl)-5-(4H-1,2,4-triazol-3-yl)-1,3-thiazol-2-yl]morpholine

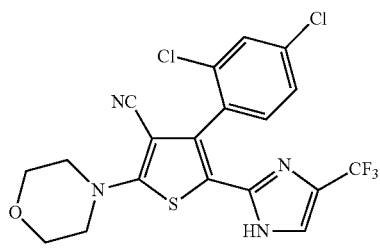 [SMILES: N#Cc1c(N2CCOCC2)sc(-c2nc(C(F)(F)F)c[nH]2)c1-c1ccc(Cl)cc1Cl]

2
4-(2,4-dichlorophenyl)-2-morpholin-4-yl-5-[4-(trifluoromethyl)-1H-imidazol-2-yl]thiophene-3-carbonitrile TABLE 1-continued

| Exemplary Compounds of formula I: |
| --- |

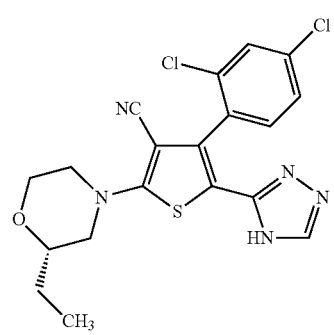 [SMILES: CC[C@H]1CN(c2sc(-c3nnc[nH]3)c(-c3ccc(Cl)cc3Cl)c2C#N)CCO1]

3
4-(2,4-dichlorophenyl)-2-[(2S)-2-ethylmorpholin-4-yl]-5-(4H-1,2,4-triazol-3-yl)thiophene-3-carbonitrile

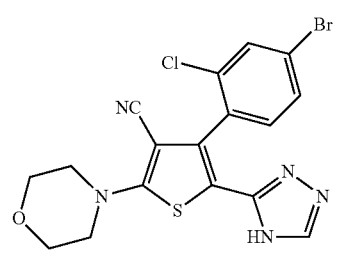 [SMILES: N#Cc1c(N2CCOCC2)sc(-c2nnc[nH]2)c1-c1ccc(Br)cc1Cl]

4
4-(4-bromo-2-chlorophenyl)-2-morpholin-4-yl-5-(4H-1,2,4-triazol-3-yl)thiophene-3-carbonitrile

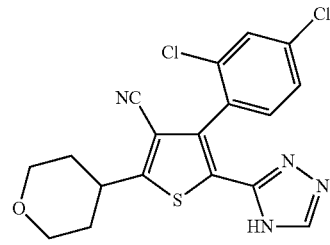 [SMILES: N#Cc1c(C2CCOCC2)sc(-c2nnc[nH]2)c1-c1ccc(Cl)cc1Cl]

5
4-(2,4-dichlorophenyl)-2-(tetrahydro-2H-pyran-4-yl)-5-(4H-1,2,4-triazol-3-yl)thiophene-3-carbonitrile

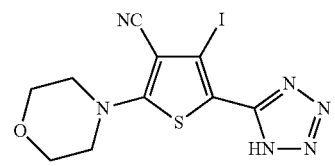 [SMILES: N#Cc1c(N2CCOCC2)sc(-c2nnn[nH]2)c1I]

6
4-iodo-2-morpholin-4-yl-5-(1H-tetrazol-5-yl)thiophene-3-carbonitrile

TABLE 1-continued

Exemplary Compounds of formula I:

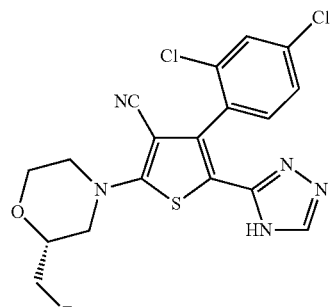

7
4-(2,4-dichlorophenyl)-2-[(2R)-2-(fluoromethyl)morpholin-4-yl]-5-(4H-1,2,4-triazol-3-yl)thiophene-3-carbonitrile

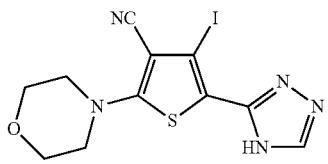 [SMILES: N#Cc1c(N2CCOCC2)sc(-c2nnc[nH]2)c1I]

8
4-iodo-2-morpholin-4-yl-5-(4H-1,2,4-triazol-3-yl)thiophene-3-carbonitrile

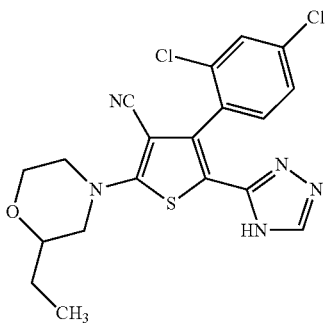 [SMILES: CCC1CN(c2sc(-c3nnc[nH]3)c(-c3ccc(Cl)cc3Cl)c2C#N)CCO1]

9
4-(2,4-dichlorophenyl)-2-(2-ethylmorpholin-4-yl)-5-(4H-1,2,4-triazol-3-yl)thiophene-3-carbonitrile

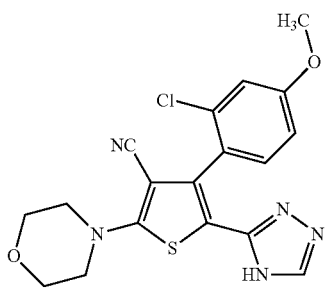 [SMILES: COc1ccc(-c2c(-c3nnc[nH]3)sc(N3CCOCC3)c2C#N)c(Cl)c1]

10
4-(2-chloro-4-methoxyphenyl)-2-morpholin-4-yl-5-(4H-1,2,4-triazol-3-yl)thiophene-3-carbonitrile TABLE 1-continued Exemplary Compounds of formula I:

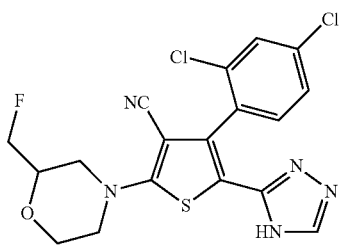 [SMILES: N#Cc1c(N2CCOC(CF)C2)sc(-c2nnc[nH]2)c1-c1ccc(Cl)cc1Cl]

11
4-(2,4-dichlorophenyl)-2-[2-(fluoromethyl)morpholin-4-yl]-5-(4H-1,2,4-triazol-3-yl)thiophene-3-carbonitrile

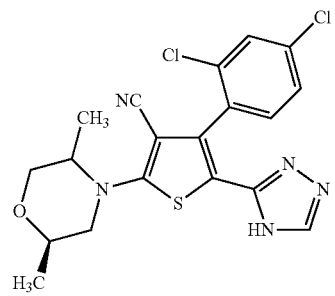 [SMILES: CC1CO[C@H](C)CN1c1sc(-c2nnc[nH]2)c(-c2ccc(Cl)cc2Cl)c1C#N]

12
4-(2,4-dichlorophenyl)-2-[(2R)-2,5-dimethylmorpholin-4-yl]-5-(4H-1,2,4-triazol-3-yl)thiophene-3-carbonitrile

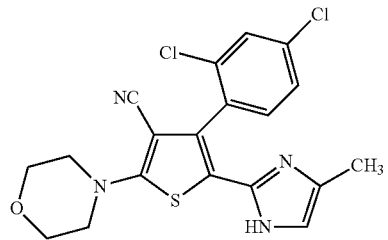 [SMILES: Cc1c[nH]c(-c2sc(N3CCOCC3)c(C#N)c2-c2ccc(Cl)cc2Cl)n1]

13
4-(2,4-dichlorophenyl)-5-(4-methyl-1H-imidazol-2-yl)-2-morpholin-4-ylthiophene-3-carbonitrile

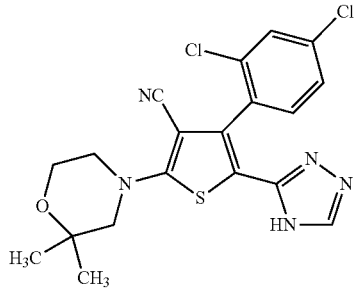 [SMILES: CC1(C)CN(c2sc(-c3nnc[nH]3)c(-c3ccc(Cl)cc3Cl)c2C#N)CCO1]

14
4-(2,4-dichlorophenyl)-2-(2,2-dimethylmorpholin-4-yl)-5-(4H-1,2,4-triazol-3-yl)thiophene-3-carbonitrile TABLE 1-continued Exemplary Compounds of formula I:

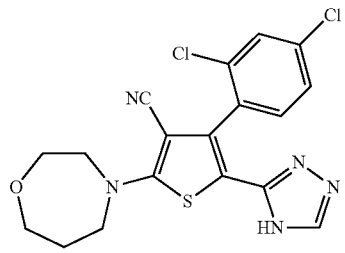 [SMILES: N#Cc1c(N2CCCOCC2)sc(-c2nnc[nH]2)c1-c1ccc(Cl)cc1Cl]

15
4-(2,4-dichlorophenyl)-2-(1,4-oxazepan-4-yl)-5-(4H-1,2,4-triazol-3-yl)thiophene-3-carbonitrile

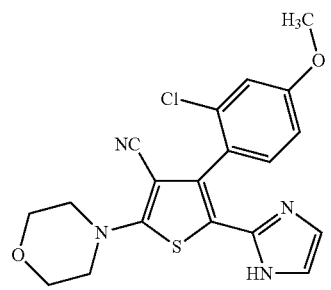 [SMILES: COc1ccc(-c2c(-c3ncc[nH]3)sc(N3CCOCC3)c2C#N)c(Cl)c1]

16
4-(2-chloro-4-methoxyphenyl)-5-(1H-imidazol-2-yl)-2-morpholin-4-ylthiophene-3-carbonitrile

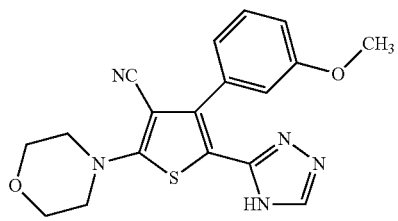 [SMILES: COc1cccc(-c2c(-c3nnc[nH]3)sc(N3CCOCC3)c2C#N)c1]

17
4-(3-methoxyphenyl)-2-morpholin-4-yl-5-(4H-1,2,4-triazol-3-yl)thiophene-3-carbonitrile

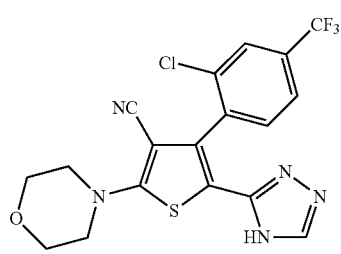 [SMILES: N#Cc1c(N2CCOCC2)sc(-c2nnc[nH]2)c1-c1ccc(C(F)(F)F)cc1Cl]

18
4-[2-chloro-4-(trifluoromethyl)phenyl]-2-morpholin-4-yl-5-(4H-1,2,4-triazol-3-yl)thiophene-3-carbonitrile TABLE 1-continued Exemplary Compounds of formula I:

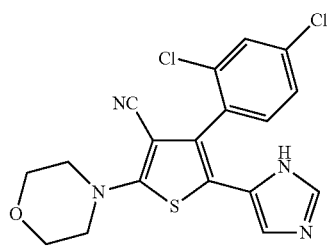 [SMILES: N#Cc1c(N2CCOCC2)sc(-c2cnc[nH]2)c1-c1ccc(Cl)cc1Cl]

19
4-(2,4-dichlorophenyl)-5-(1H-imidazol-5-yl)-2-morpholin-4-ylthiophene-3-carbonitrile

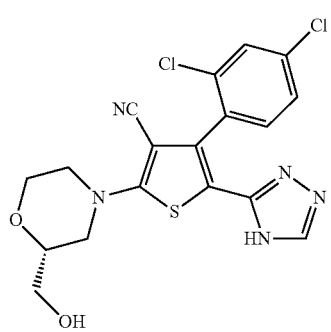 [SMILES: N#Cc1c(N2CCO[C@@H](CO)C2)sc(-c2nnc[nH]2)c1-c1ccc(Cl)cc1Cl]

20
4-(2,4-dichlorophenyl)-2-[(2R)-2-(hydroxymethyl)morpholin-4-yl]-5-(4H-1,2,4-triazol-3-yl)thiophene-3-carbonitrile

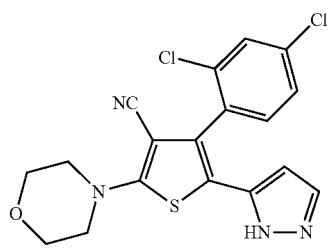 [SMILES: N#Cc1c(N2CCOCC2)sc(-c2ccn[nH]2)c1-c1ccc(Cl)cc1Cl]

21
4-(2,4-dichlorophenyl)-2-morpholin-4-yl-5-(1H-pyrazol-5-yl)thiophene-3-carbonitrile

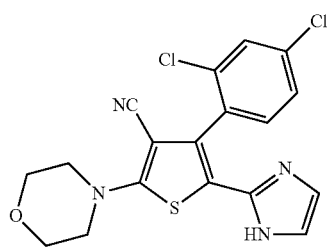 [SMILES: N#Cc1c(N2CCOCC2)sc(-c2ncc[nH]2)c1-c1ccc(Cl)cc1Cl]

22
4-(2,4-dichlorophenyl)-5-(1H-imidazol-2-yl)-2-morpholin-4-ylthiophene-3-carbonitrile TABLE 1-continued Exemplary Compounds of formula I:

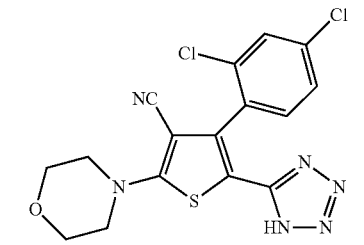 [SMILES: N#Cc1c(N2CCOCC2)sc(-c2nnn[nH]2)c1-c1ccc(Cl)cc1Cl]

23
4-(2,4-dichlorophenyl)-2-morpholin-4-yl-5-
(1H-tetrazol-5-yl)thiophene-3-carbonitrile

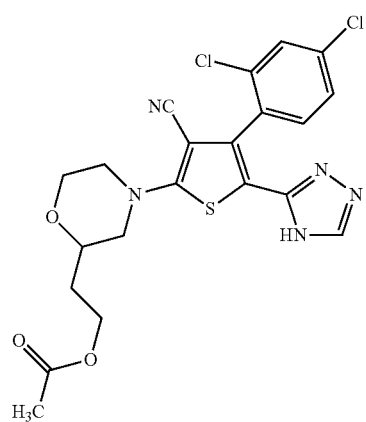 [SMILES: CC(=O)OCCC1CN(c2sc(-c3nnc[nH]3)c(-c3ccc(Cl)cc3Cl)c2C#N)CCO1]

24
2-{4-[3-cyano-4-(2,4-dichlorophenyl)-5-(4H-
1,2,4-triazol-3-yl)-2-thienyl]morpholin-2-
yl}ethyl acetate

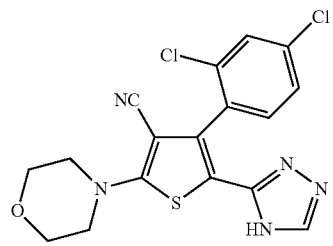 [SMILES: N#Cc1c(N2CCOCC2)sc(-c2nnc[nH]2)c1-c1ccc(Cl)cc1Cl]

25
4-(2,4-dichlorophenyl)-2-morpholin-4-yl-5-
(4H-1,2,4-triazol-3-yl)thiophene-3-
carbonitrile

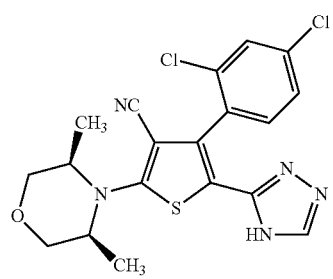 [SMILES: C[C@@H]1COC[C@H](C)N1c1sc(-c2nnc[nH]2)c(-c2ccc(Cl)cc2Cl)c1C#N]

26
4-(2,4-dichlorophenyl)-2-[(3R,5S)-3,5-
dimethylmorpholin-4-yl]-5-(4H-1,2,4-triazol-
3-yl)thiophene-3-carbonitrile TABLE 1-continued Exemplary Compounds of formula I:

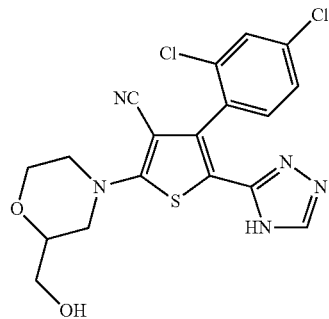 [SMILES: N#Cc1c(N2CCOC(CO)C2)sc(-c2nnc[nH]2)c1-c1ccc(Cl)cc1Cl]

27
4-(2,4-dichlorophenyl)-2-[2-
(hydroxymethyl)morpholin-4-yl]-5-(4H-
1,2,4-triazol-3-yl)thiophene-3-carbonitrile

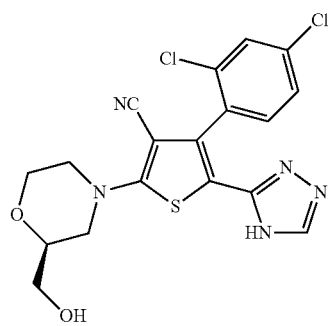 [SMILES: N#Cc1c(N2CCO[C@H](CO)C2)sc(-c2nnc[nH]2)c1-c1ccc(Cl)cc1Cl]

28
4-(2,4-dichlorophenyl)-2-[(2S)-2-
(hydroxymethyl)morpholin-4-yl]-5-(4H-
1,2,4-triazol-3-yl)thiophene-3-carbonitrile

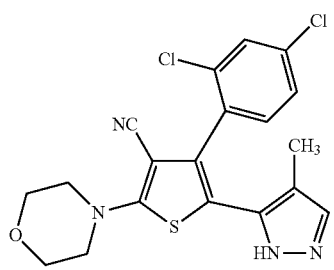 [SMILES: Cc1cn[nH]c1-c1sc(N2CCOCC2)c(C#N)c1-c1ccc(Cl)cc1Cl]

29
4-(2,4-dichlorophenyl)-5-(4-methyl-1H-
pyrazol-5-yl)-2-morpholin-4-ylthiophene-3-
carbonitrile

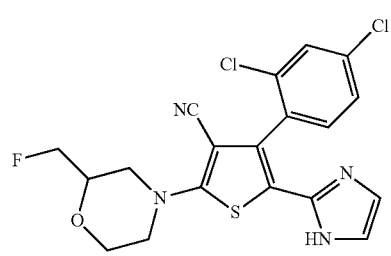 [SMILES: N#Cc1c(N2CCOC(CF)C2)sc(-c2ncc[nH]2)c1-c1ccc(Cl)cc1Cl]

30
4-(2,4-dichlorophenyl)-2-[2-
(fluoromethyl)morpholin-4-yl]-5-(1H-
imidazol-2-yl)thiophene-3-carbonitrile TABLE 1-continued Exemplary Compounds of formula I:

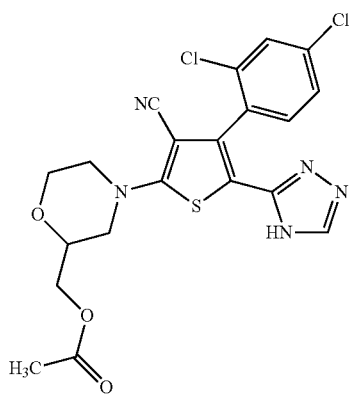 [SMILES: CC(=O)OCC1CN(c2sc(-c3nnc[nH]3)c(-c3ccc(Cl)cc3Cl)c2C#N)CCO1]

31
{4-[3-cyano-4-(2,4-dichlorophenyl)-5-(4H-
1,2,4-triazol-3-yl)-2-thienyl]morpholin-2-
yl}methyl acetate

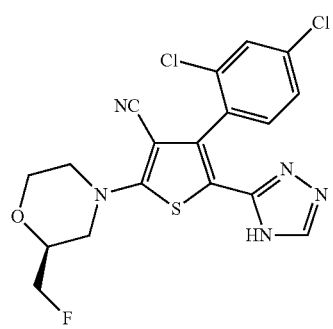 [SMILES: N#Cc1c(N2CCO[C@H](CF)C2)sc(-c2nnc[nH]2)c1-c1ccc(Cl)cc1Cl]

32
4-(2,4-dichlorophenyl)-2-[(2S)-2-
(fluoromethyl)morpholin-4-yl]-5-(4H-1,2,4-
triazol-3-yl)thiophene-3-carbonitrile

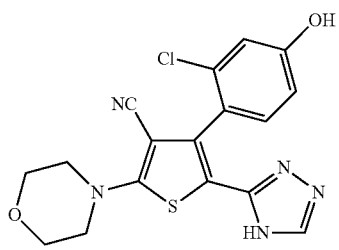 [SMILES: N#Cc1c(N2CCOCC2)sc(-c2nnc[nH]2)c1-c1ccc(O)cc1Cl]

33
4-(2-chloro-4-hydroxyphenyl)-2-morpholin-
4-yl-5-(4H-1,2,4-triazol-3-yl)thiophene-3-
carbonitrile

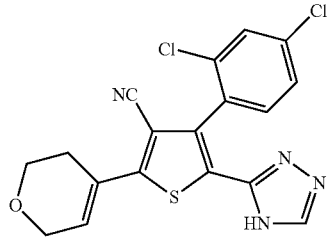 [SMILES: N#Cc1c(C2=CCOCC2)sc(-c2nnc[nH]2)c1-c1ccc(Cl)cc1Cl]

34
4-(2,4-dichlorophenyl)-2-(3,6-dihydro-2H-
pyran-4-yl)-5-(4H-1,2,4-triazol-3-
yl)thiophene-3-carbonitrile

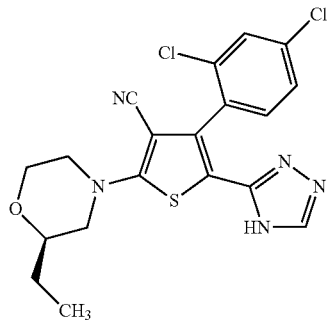 [SMILES: CC[C@@H]1CN(c2sc(-c3nnc[nH]3)c(-c3ccc(Cl)cc3Cl)c2C#N)CCO1]

35
4-(2,4-dichlorophenyl)-2-[(2R)-2-
ethylmorpholin-4-yl]-5-(4H-1,2,4-triazol-3-
yl)thiophene-3-carbonitrile

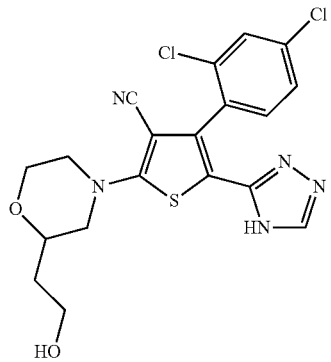 [SMILES: N#Cc1c(N2CCOC(CCO)C2)sc(-c2nnc[nH]2)c1-c1ccc(Cl)cc1Cl]

36
4-(2,4-dichlorophenyl)-2-[2-(2-
hydroxyethyl)morpholin-4-yl]-5-(4H-1,2,4-
triazol-3-yl)thiophene-3-carbonitrile 4 General Synthetic Methods and Intermediates:

The compounds of the present invention can be prepared by methods known to one of ordinary skill in the art and/or by reference to the schemes shown below and the synthetic examples that follow. Exemplary synthetic routes are set forth in Schemes 1-11 below, and in the Examples.

Scheme 1: General route for the synthesis of 3-substituted 4-cyano-5-morpholin-4-ylthiophene-2-triazoles

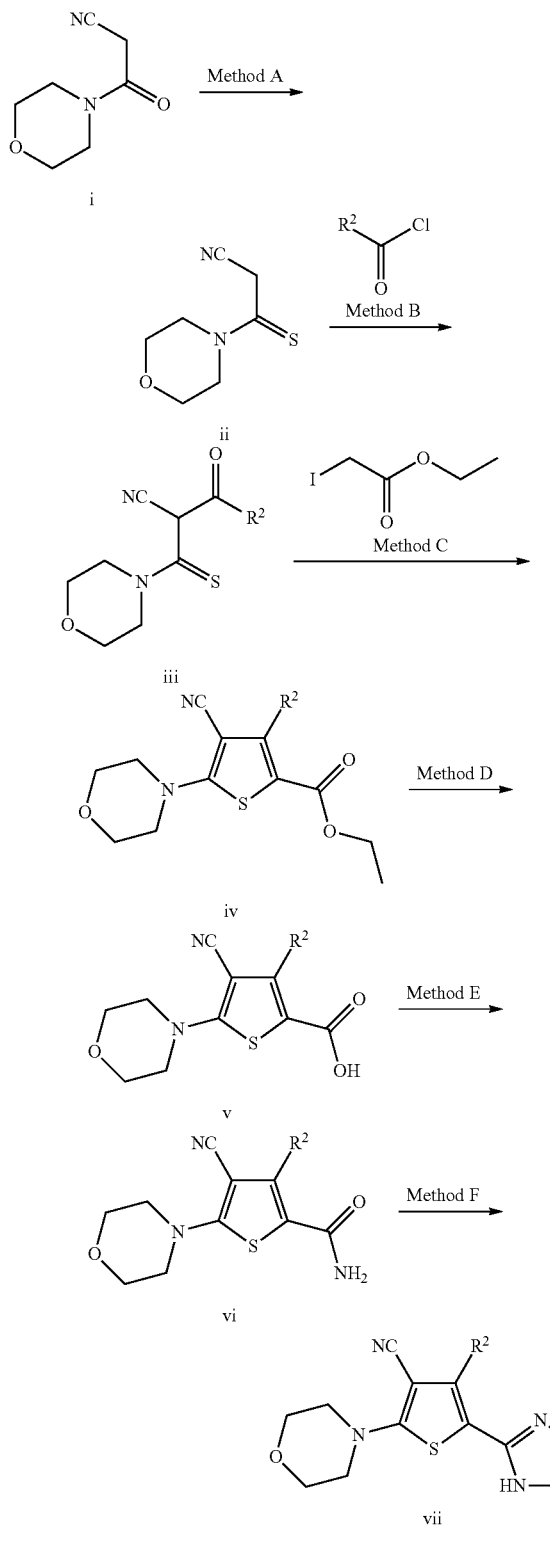

Scheme 1 above shows a general route for preparing compounds of formula (vii). As shown in Scheme 1, conversion of amide i to thioamide ii can be accomplished using a suitable reagent, such as Lawesson's reagent, in THF (Method A).

Thioamide ii can be coupled with acyl chlorides in the presence of an appropriate base, such as DIPEA, in ACN (Method B) to afford compounds of formula iii, that can be subsequently coupled with a suitable α-haloacetate ester, such as iodoethylacetate or bromoethylacetate in a one-pot process using microwave irradiation to afford substituted thiophenes iv (Method C). Esters iv can be hydrolyzed using a suitable base, such as NaOH in aqueous conditions using cosolvents, such as THF and MeOH to afford carboxylic acids v (Method D). Amides vi can be obtained by coupling of compounds v with ammonia using a suitable coupling reagent, such as EDCI and HOBT in DCM (Method E). Treatment of compounds vi with DMFDMA under microwave irradiation gives intermediate enamines, that are transformed to triazoles vii using hydrazine in acetic acid under microwave irradiation.

Scheme 2: Alternative synthesis of 3-substituted 4-cyano-5-morpholin-4-ylthiophene-2-triazoles

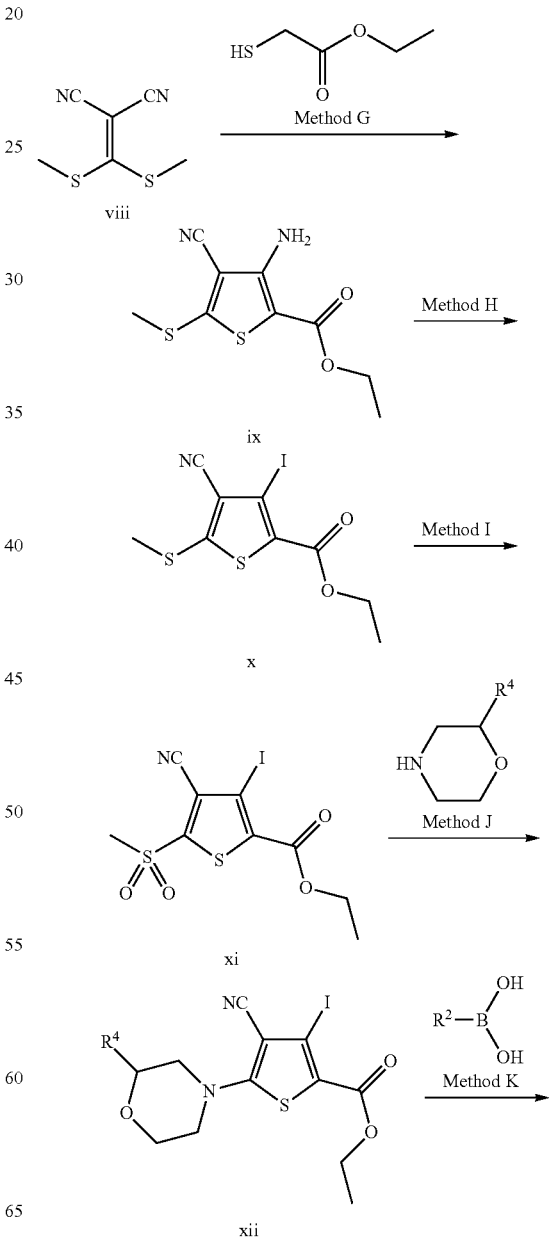

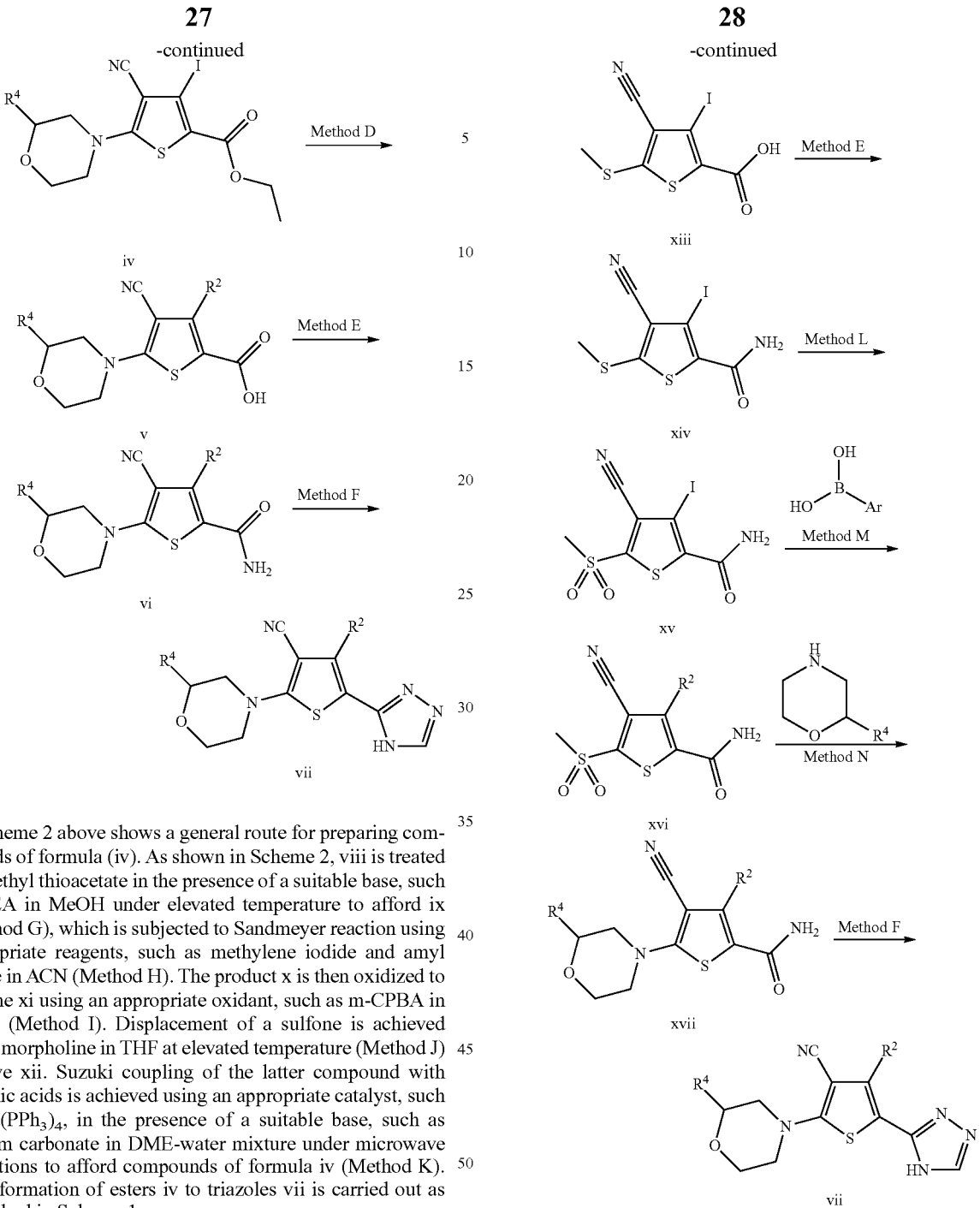

Scheme 2 above shows a general route for preparing compounds of formula (iv). As shown in Scheme 2, viii is treated with ethyl thioacetate in the presence of a suitable base, such as TEA in MeOH under elevated temperature to afford ix (Method G), which is subjected to Sandmeyer reaction using appropriate reagents, such as methylene iodide and amyl nitrite in ACN (Method H). The product x is then oxidized to sulfone xi using an appropriate oxidant, such as m-CPBA in DCM (Method I). Displacement of a sulfone is achieved using morpholine in THF at elevated temperature (Method J) to give xii. Suzuki coupling of the latter compound with boronic acids is achieved using an appropriate catalyst, such as Pd(PPh$_3$)$_4$, in the presence of a suitable base, such as sodium carbonate in DME-water mixture under microwave conditions to afford compounds of formula iv (Method K). Transformation of esters iv to triazoles vii is carried out as described in Scheme 1.

Scheme 3:
Alternative route for the synthesis of substituted 4-cyano-3-aryl-5-(morpholine-4-yl)thiophene-2-carboxamides

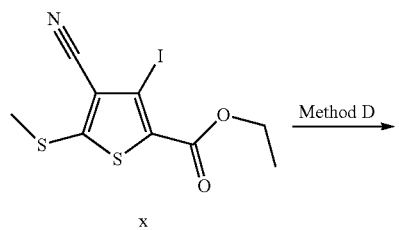

Scheme 3 above shows a general route for preparing compounds of formula (xvii). As shown in Scheme 3, ester x is hydrolyzed using a suitable base, such as sodium hydroxide in aqueous conditions, to give carboxylic acid xiii (Method D). Formation of amide xiv is done using an appropriate coupling reagent, such as EDCI and HOBT in DCM followed by treatment with aqueous ammonia (Method E). Thioether xiv can be oxidized to sulfone xv using a suitable oxidant, such as mCPBA in DCM (Method L). The latter compound is subjected to Suzuki coupling conditions with an appropriate combination of aryl boronic acid, Pd source, such as Pd(dba)$_2$, ligand, such as dpePhos, and a base, such as potassium phosphate in DME/DMA solvent mixture under microwave irradiation to afford advanced intermediate of formula xvi (Method M). Treatment of sulfones xvi with neat substituted morpholines under elevated temperature affords amides of formula xvii (Method N). Transformation of amides xvii to triazoles vii is carried out as described in Scheme 1.

Scheme 4:
General route for the synthesis of 3-substituted 4-cyano-5-morpholin-4-ylthiophene-2-imidazoles

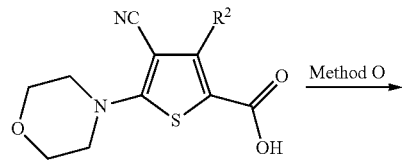

v

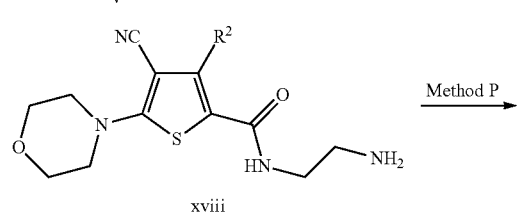

xviii

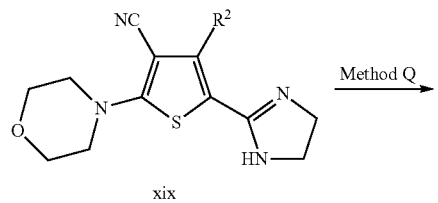

xix

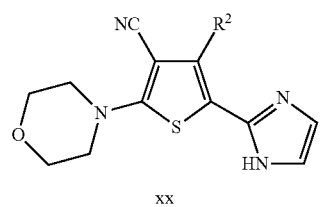

xx

Scheme 4 above shows a general route for preparing compounds of formula (xx). As shown in Scheme 4, acid v is treated with Boc protected ethylenediamine using standard coupling conditions, such as EDCI and HOBt in DCM. Protective group is removed using an appropriate acid, for example TFA in DCM to give amide xviii (Method O). Cyclization of xviii is achieved using suitable conditions, for example POCl₃ (Method P) and the formed dihydroimidazole xix is oxidized to imidazole xx using a suitable oxidative method, such as Swern oxidation (Method Q).

Scheme 5: Alternative synthesis of 3-substituted 4-cyano-5-morpholin-4-ylthiophene-2-imidazoles

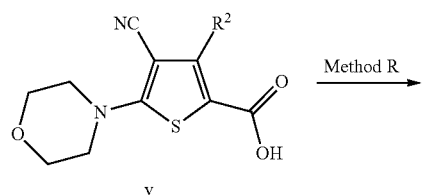

v

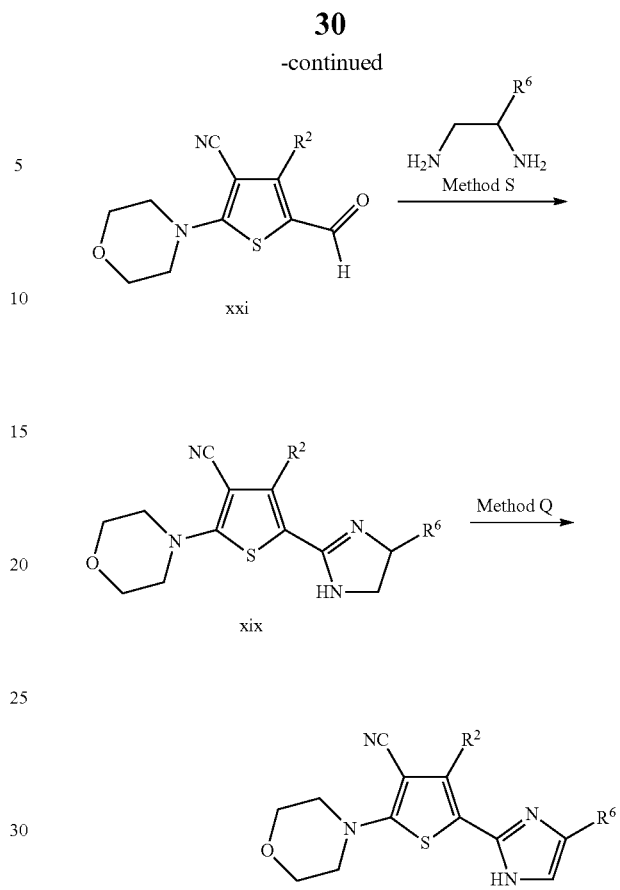

Scheme 5 above shows an alternative route for preparing compounds of formula (xx). As shown in Scheme 5, acid v is transformed to an aldehyde using a suitable synthetic sequence, for example through a coupling with N,O-dimethylhydroxylamine and subsequent reduction of the formed Weinreb amide with DIBAL (Method R). Aldehyde xxi is then treated with diamine and iodine (Method S) to form dihydroimidazole xix, which is oxidized to imidazole xx using a suitable oxidating method, such as Swern oxidation (Method Q).

Scheme 6:
General route for the synthesis of 3-substituted 4-cyano-5-morpholin-4-ylthiophene-2-imidazoles

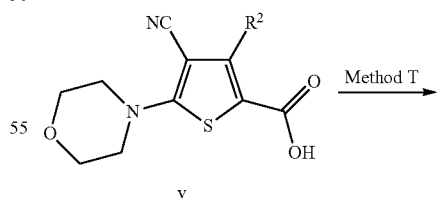

v

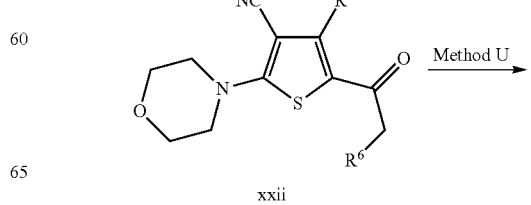

xxii

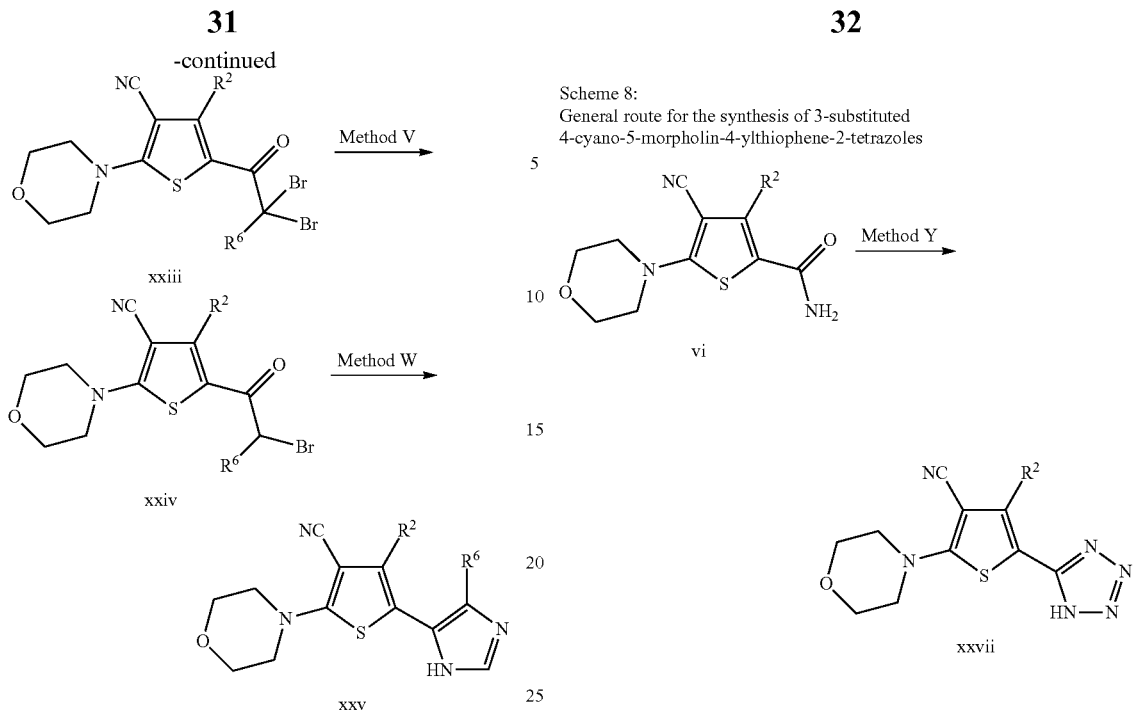

Scheme 6 above shows an alternative route for preparing compounds of formula (xxv). As shown in Scheme 6, acid v is transformed to a ketone using a suitable synthetic sequence, for example through a coupling with N,O-dimethylhydroxylamine and subsequent treatment of the formed Weinreb amide with alkyllithium reagent (Method T). Ketone xxii is then treated with bromine in acetic acid under microwave irradiation (Method U) to form dibromoketone xxiii, which is reduced to bromoketone xxiv using a suitable method, such as diethyl phosphate and a base, such as TEA (Method V). Treatment of xxiv with formamide under microwave irradiation affords the final imidazole xxv (Method W).

Scheme 7:
General route for the synthesis of 3-substituted 4-cyano-5-morpholin-4-ylthiophene-2-pyrazoles

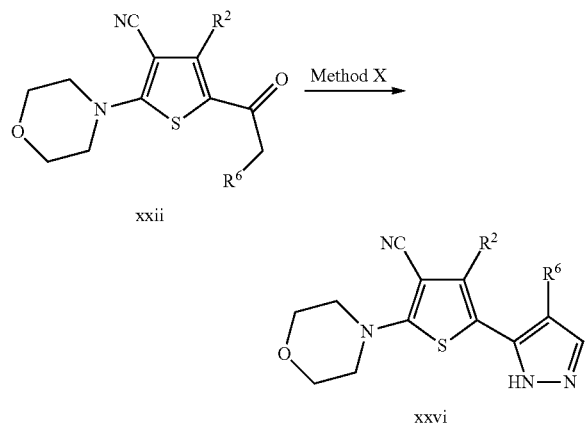

Scheme 7 above shows a general route for preparing compounds of formula (xxvi). As shown in Scheme 7, ketone xxii is treated with DMFDMA to afford an intermediate enamine followed by reaction with hydrazine hydrate in a suitable solvent, for example acetic acid to give pyrazole xxvi (Method X).

Scheme 8 above shows a general route for preparing compounds of formula (xxvii). As shown in Scheme 8, amide vi is treated with an azide source, for example sodium azide using a suitable Lewis acid, for example silicon tetrachloride in an appropriate solvent, such as acetonitrile to give tetrazole xxvii (Method Y).

Scheme 9: General route for the synthesis of 3-substituted 4-cyano-5-dihydropyran-4-ylthiophene-2-triazoles

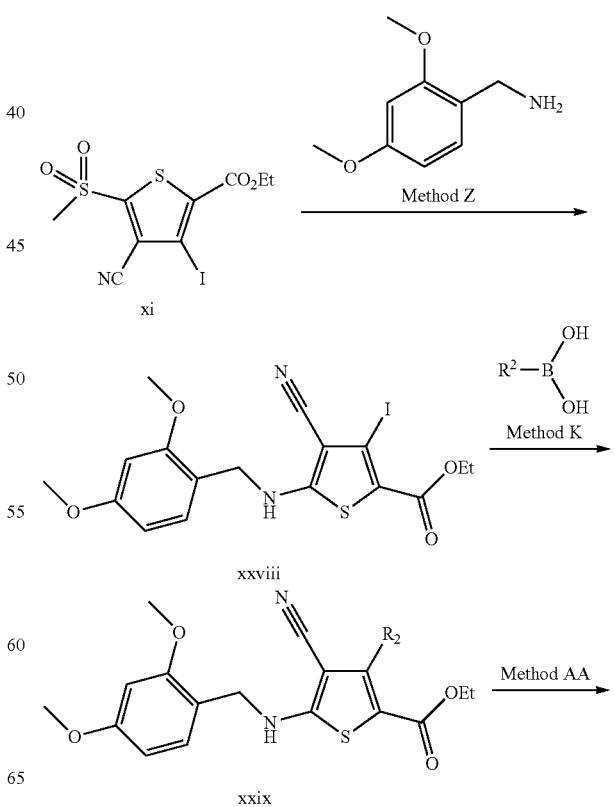

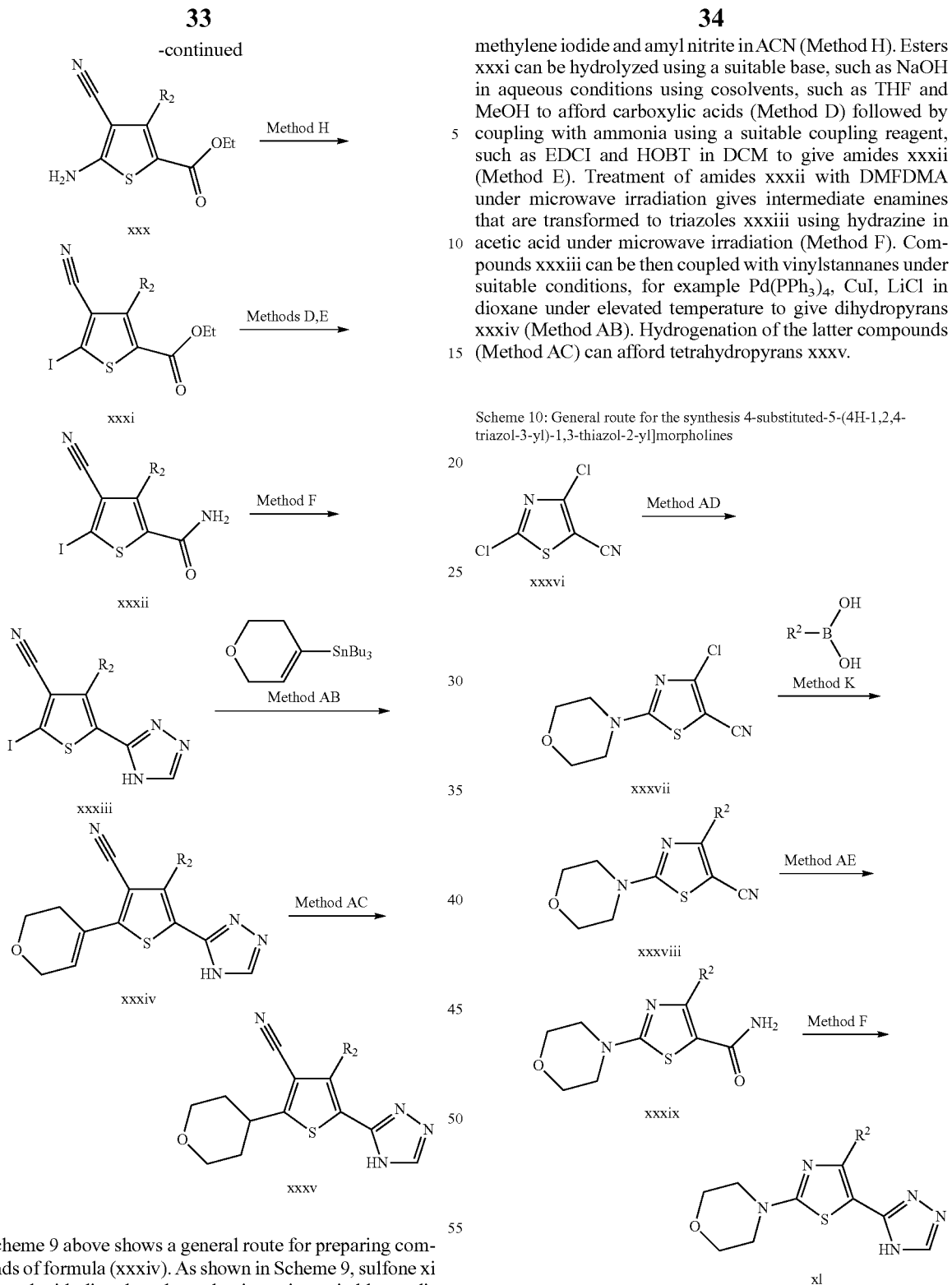

methylene iodide and amyl nitrite in ACN (Method H). Esters xxxi can be hydrolyzed using a suitable base, such as NaOH in aqueous conditions using cosolvents, such as THF and MeOH to afford carboxylic acids (Method D) followed by coupling with ammonia using a suitable coupling reagent, such as EDCI and HOBT in DCM to give amides xxxii (Method E). Treatment of amides xxxii with DMFDMA under microwave irradiation gives intermediate enamines that are transformed to triazoles xxxiii using hydrazine in acetic acid under microwave irradiation (Method F). Compounds xxxiii can be then coupled with vinylstannanes under suitable conditions, for example Pd(PPh$_3$)$_4$, CuI, LiCl in dioxane under elevated temperature to give dihydropyrans xxxiv (Method AB). Hydrogenation of the latter compounds (Method AC) can afford tetrahydropyrans xxxv.

Scheme 10: General route for the synthesis 4-substituted-5-(4H-1,2,4-triazol-3-yl)-1,3-thiazol-2-yl]morpholines Scheme 9 above shows a general route for preparing compounds of formula (xxxiv). As shown in Scheme 9, sulfone xi is treated with dimethoxybenzylamine using suitable conditions, for example TEA in THF at elevated temperature. Suzuki coupling of the latter compound with boronic acids is achieved using an appropriate catalyst, such as Pd(PPh$_3$)$_4$, in the presence of a suitable base, such as sodium carbonate in DME-water mixture under microwave conditions to afford compounds of formula xxix (Method K). Deprotection of dimethoxybenzyl group is achieved with a suitable acid, such as TFA in DCM (Method AA). Amines xxx are then subjected to Sandmeyer reaction using appropriate reagents, such as Scheme 10 above shows a general route for preparing compounds of formula (xl). As shown in Scheme 10, 2,4-dichlorothiazole-5-carbonitrile is transformed to xxxvii by treatment with morpholine (Method AD), which in turn is subjected to Suzuki coupling under microwave conditions using standard reagents, for example Pd(PPh$_3$)$_2$Cl$_2$, sodium carbonate in DME-ethanol-water mixture (Method K) to afford compounds of formula xxxviii. Hydrolysis of the nitrile group is achieved using a strong acid, such as sulfuric acid (Method AE) to give amides xxxix, which are transformed to triazoles xl using a two step procedure involving treatment with DMFDMA under microwave irradiation followed by hydrazine in acetic acid under microwave irradiation (Method F).

Scheme 11:
General route for the synthesis of substituted furanes and pyrroles

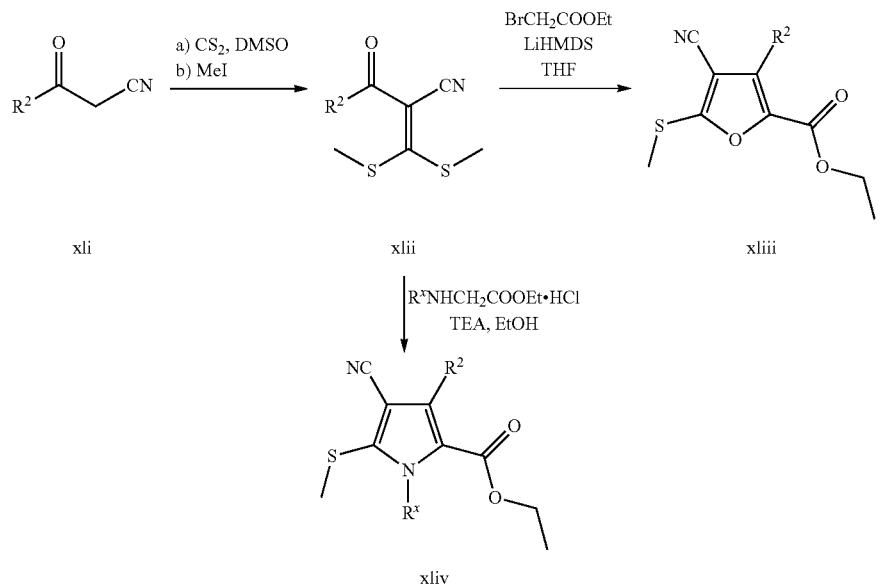

Compounds of formula (I), where X=O or X=N(R) can be prepared from compounds xliii. The synthesis of compounds of formula xliii is reported in the literature (Fernandez, M.-C.; Castano, A.; Dominguez, E.; Escribano, A.; Jiang, D.; Jimenez, A.; Hong, E.; Hornback, W. J.; Nisenbaum, E. S.; Rankl, N.; Tromiczak, E.; Vaught, G.; Zarrinmayeh, H.; Zimmerman, D. M. *Bioorg. Med. Chem. Lett.*, 2006, 66, 5057-5061), and is outlined in Scheme 11. Deprotonation of propionitriles xli followed by condensation with carbon disulfide and subsequent quenching with methyl iodide gives compounds of formula xlii. These compounds can be further converted to furan ethyl carboxylates xliii by cyclocondensation with bromoethyl acetate. Similarly, treatment of xlii with N-alkyl glycine esters affords alkylated pyrrole ethyl carboxylates xliv. Compounds of formula xliii and xliv can be further elaborated as described in Schemes 1-9 above.

5. Uses, Formulation and Administration

As discussed above, the present invention provides compounds that are useful as inhibitors of PI3K enzymes, and thus the present compounds are useful for treating proliferative, inflammatory, or cardiovascular disorders such as tumor and/or cancerous cell growth mediated by PI3K. In particular, the compounds are useful in the treatment of cancers in a subject, including, but not limited to, lung and bronchus, prostate, breast, pancreas, colon and recum, thyroid, liver and intrahepatic bile duct, hepatocellular, gastric, glioma/glioblastoma, endometrial, melanoma, kidney, and renal pelvis, urinary bladder, utering corpus, uterine cervix, ovary, multiple myeloma, esophagus, acute myelogenous leukemia, chronic myelogenous leukemia, lymphocytic leukemia, myeloid leukemia, brain, oral cavity, and pharynx, small intestine, non-Hodgkin lymphoma, and villous colon adenoma.

In some embodiments, compounds of the invention are suitable for the treatment of breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of PI3K.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PI3K and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of PI3K. In some embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Another aspect of the invention relates to inhibiting PI3K, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where PI3K kinase plays a role.

EXPERIMENTAL PROCEDURES

I. Preparation of Exemplary Compounds:
Definitions
AcOH acetic acid
ACN acetonitrile
ATP adenosine triphosphate
BCA bicinchoninic acid
BSA bovine serum albumin
BOC tert-butoxycarbonyl
m-CPBA m-chloroperbenzoic acid
DCE dichloroethane
DCM dichloromethane
DDQ 2,3-dichloro-5,6-dicyano-1,4-benzoquinone
DIPEA diisopropylethyl amine
DMEM Dulbecco's Modified Eagle's Medium
DMF N,N-dimethylformamide
DMFDMA N,N-dimethylformamide dimethyl acetal
DMSO dimethylsulfoxide
DPPA diphenylphosphoryl azide
DTT dithiothreitol
dppf diphenylphosphinoferrocene
EDCI N-(3-dimethylaminopropyl)-N'-ethylcarbodiimide hydrochloride
EDTA ethylenediaminetetraacetic acid
EtOAc ethyl acetate
EtOH ethanol
FA formic acid
FBS fetal bovine serum
h hours
HATU N,N,N',N'-tetramethyl-o-(7-azabenzotriazole-1-yl) uronium hexafluorophosphate
HBTU o-benzotriazol-1-yl-N,N,N',N'-tetramethyluronium hexafluorophosphate
HEPES N-(2-Hydroxyethyl)piperazine-N'-(2-ethanesulfonic acid)
HOBT 1-hydroxybenztriazole hydrate
HRMS high resolution mass spectrum
LAH lithium aluminum hydride
LCMS liquid chromatography mass spectrum
m/z mass to charge
Me methyl
MeOH methanol
min minutes
MS mass spectrum
MTT methylthiazoletetrazolium
MWI microwave irradiation
PBS phosphate buffered saline
PKA cAMP-dependent protein kinase
rt room temperature
TEA triethylamine
TFFA trifluoroacetic anhydride
THF tetrahydrofuran
TMB 3,3',5,5'-Tetramethylbenzidine
WST (4-[3-(4-iodophenyl)-2-(4-nitrophenyl)-2H-5-tetrazolio]-1,3-benzene disulfonate sodium salt)
Analytical LC-MS Methods
LCMS Conditions Spectra were run on a Phenominex Luna 5 μm C18 50×4.6 mm column on a Hewlett-Packard HP1100 using the following gradients:

Method Formic Acid (FA): Acetonitrile containing 0 to 100 percent 0.1% formic acid in water (2.5 ml/min for a 3 minute run).

Method Ammonium Acetate (AA): Acetonitrile containing 0 to 100 percent 10 mM ammonium acetate in water (2.5 ml/min for a 3 minute run).

EXAMPLE 1

Synthesis of 4-(2,4-dichlorophenyl)-2-morpholin-4-yl-5-(4H-1,2,4-triazol-3-yl)thiophene-3-carbonitrile (Compound I-25)

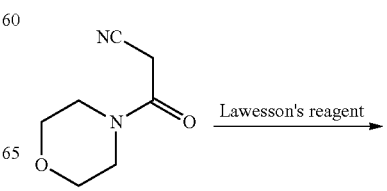

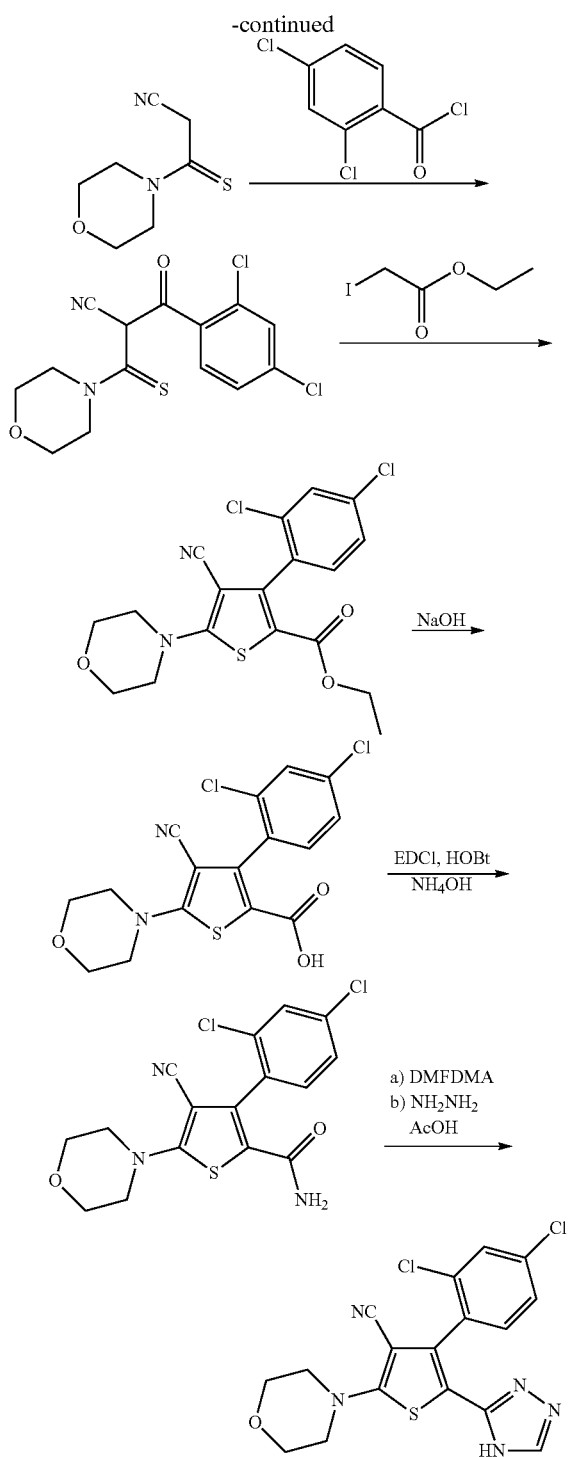

Step 1: 3-morpholin-4-yl-3-thioxopropanenitrile

To a solution of 3-morpholin-4-yl-3-oxopropanenitrile (3.0 g, 19.5 mmol) in anhydrous THF (45 mL) was added Lawesson's reagent (4.2 g, 10.3 mmol). The reaction mixture was allowed to stir at rt for 16 h and was then concentrated to small volume. A solid precipitated and was filtered. The solid was washed with diethyl ether to give 3-morpholin-4-yl-3-thioxopropanenitrile (2.3 g, 70%). LCMS: (AA) ES+ 171.2. $^1$H NMR (400 MHz, $d_1$-chloroform) δ: 4.29-4.27 (m, 2H), 4.00 (s, 2H) and 3.83-3.81 (m, 6H).

Step 2 and 3: Ethyl 4-cyano-3-(2,4-dichlorophenyl)-5-morpholin-4-ylthiophene-2-carboxylate A solution of 3-morpholin-4-yl-3-thioxopropanenitrile (0.150 g, 0.88 mmol) in anhydrous ACN (1.2 mL) was cooled to 0° C. To this cooled solution was added of 2,4-dichlorobenzoyl chloride (0.149 mL, 1.06 mmol) and DIPEA (0.161 mL, 0.93 mmol). The mixture was allowed to stir at rt under nitrogen for 15 min before ethyl iodoacetate (0.110 mL, 0.93 mmol) and DIPEA (0.161 mL, 0.93 mmol) were added. The reaction mixture was subjected to MWI at 140° C. for 10 min. The mixture was allowed to cool and was concentrated. The residue was purified by column chromatography to give ethyl 4-cyano-3-(2,4-dichlorophenyl)-5-morpholin-4-ylthiophene-2-carboxylate (0.1 g, 28%). LCMS: (AA) ES+ 411. $^1$H NMR (400 MHz, $d_1$-chloroform) δ: 7.49 (d, 1H), 7.33 (dd, 1H), 7.20 (d, 1H), 4.16-4.08 (m, 2H), 3.89-3.85 (m, 4H), 3.66-3.63 (m, 4H) and 1.12 (t, 3H).

Step 4: 4-cyano-3-(2,4-dichlorophenyl)-5-morpholin-4-ylthiophene-2-carboxylic acid To a solution of ethyl 4-cyano-3-(2,4-dichlorophenyl)-5-morpholin-4-ylthiophene-2-carboxylate (0.060 g, 0.15 mmol) in THF/MeOH/water (2:1:2) (5 mL) was added sodium hydroxide (0.061 g, 1.5 mmol). The reaction mixture was allowed to stir at rt for 20 h and was concentrated. The residue was acidified with 1N HCl and was extracted with EtOAc. The organic solutions were combined, washed with brine, dried over MgSO$_4$, filtered and concentrated to give 4-cyano-3-(2,4-dichlorophenyl)-5-morpholin-4-ylthiophene-2-carboxylic acid (0.034 g, 62%). LCMS: (FA) ES+ 382.9. $^1$H NMR (400 MHz, $d_6$-DMSO) δ: 7.75 (d, 1H), 7.50 (dd, 1H), 7.39 (d, 1H), 3.79-3.74 (m, 4H) and 3.61-3.55 (m, 4H).

Step 5: 4-cyano-3-(2,4-dichlorophenyl)-5-morpholin-4-ylthiophene-2-carboxamide

4-Cyano-3-(2,4-dichlorophenyl)-5-morpholin-4-ylthiophene-2-carboxylic acid (0.050 g, 0.13 mmol), HOBT (0.037 g, 0.274 mmol) and EDCI (50 mg, 0.261 mmol) were suspended in DCM (6.5 mL). After 30 min the reagents dissolved. To the resulting solution was added concentrated aqueous ammonia (0.26 mL, 6.5 mmol) and the solution was allowed to stir vigorously at rt overnight. The reaction mixture was concentrated and the residue was diluted with 1N HCl and extracted with EtOAc. The organic solutions were combined, washed with sat NaHCO$_3$ and brine, dried over MgSO$_4$ filtered and concentrated to give a brown solid. The solid was triturated with hexanes and cold EtOAc to give 4-cyano-3-(2,4-dichlorophenyl)-5-morpholin-4-ylthiophene-2-carboxamide (0.024 g, 49%). LCMS: (AA) ES+ 382, ES− 380. $^1$H NMR (400 MHz, $d_6$-DMSO) δ: 7.78 (s, 1H), 7.54 (d, 2H), 7.43 (d, 2H), 3.79-3.77 (m, 4H) and 3.55-3.52 (m, 4H).

Step 6: Synthesis of 4-(2,4-dichlorophenyl)-2-morpholin-4-yl-5-(4H-1,2,4-triazol-3-yl)thiophene-3-carbonitrile A mixture of 4-cyano-3-(2,4-dichlorophenyl)-5-morpholin-4-ylthiophene-2-carboxamide (31.6 mg, 0.0000827 mol) in 1,1-dimethoxy-N,N-dimethylmethanamine (1.0 mL, 0.0075 mol) was flushed with argon and then irradiated in microwave at 160° C. for 60 min. The reaction mixture was concentrated to give 4-cyano-3-(2,4-dichlorophenyl)-N-((dimethylamino)methylene)-5-morpholinothiophene-2-carboxamide as intermediate (31 mg, 86%). LCMS: (FA) ES+ 437.13. $^1$H NMR (400 MHz, $d_6$-DMSO) δ: 8.34 (s, 1H), 7.69 (d, 1H), 7.47 (d, 1H), 7.33 (d, 1H), 3.79-3.74 (m, 4H), 3.59-3.54 (m, 4H), 3.07 (s, 3H), 2.72 (s, 3H). To the above intermediate in AcOH (1.8 mL, 0.032 mol) was added hydrazine hydrate (50 mg, 0.001 mol). The mixture was flushed with argon and then irradiated in microwave at 120° C. for 20 min. The mixture was concentrated to remove most of the solvent. Water was added to the residue and the precipitate was collected, washed with water, dried to afford 4-(2,4-dichlorophenyl)-2-morpholino-5-(4H-1,2,4-triazol-3-yl)thiophene-3-carbonitrile (12.8 mg, 55%). LCMS: (FA) ES+ 406.11, ES− 404.21, $^1$H NMR (400 MHz, $d_6$-DMSO) δ: 14.00 (s, 1H), 8.43 (s, 1H), 7.74 (d, 1H), 7.49 (d, 1H), 7.41 (d, 1H), 3.82-3.76 (m, 4H), 3.56-3.51 (m, 4H).

Compounds in the following table were prepared from the appropriate starting materials in a method analogous to that of Example 1:

| | |
|---|---|
| 4 | LCMS: (FA) ES+ 449.95. |
| 8 | LCMS: (FA) ES+ 387.99. |
| 10 | LCMS: (FA) ES+ 402. |
| 12 | LCMS: (FA) ES+ 434. |
| 18 | LCMS: (FA) ES+ 440.14. |
| 26 | LCMS: (FA) ES+ 434. |

EXAMPLE 2

4-(2,4-dichlorophenyl)-2-(2-(fluoromethyl)morpholino)-5-(4H-1,2,4-triazol-3-yl)thiophene-3-carbonitrile (Compound I-11)

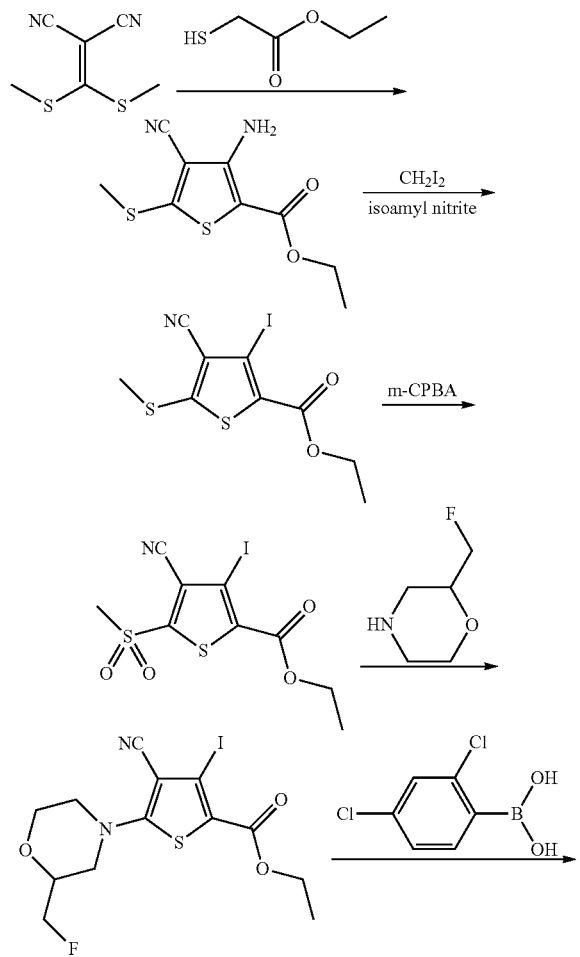

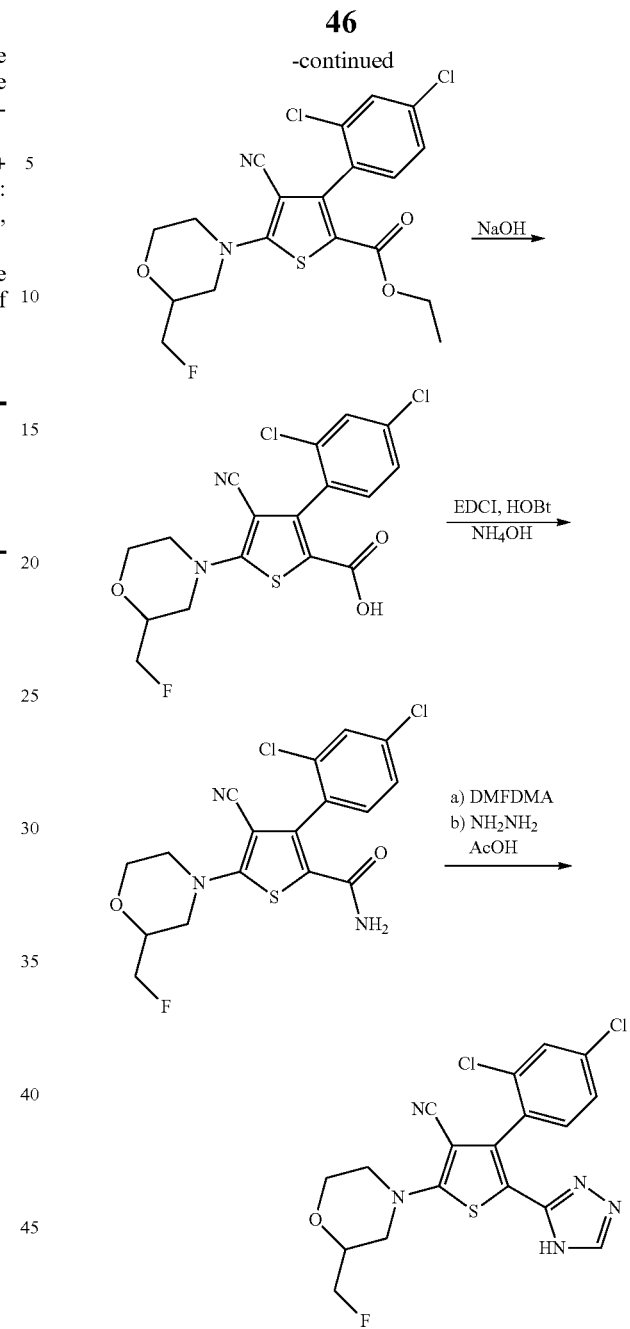

Step 1: Ethyl 3-amino-4-cyano-5-(methylsulfanyl)thiophene-2-carboxylate

A mixture of [bis(methylsulfanyl)methylene]malononitrile (40 g, 230 mmol), ethylthioglycolate (29 g, 230 mmol) and TEA (24 mL, 173 mmol) in MeOH (600 mL) was allowed to stir at reflux for 2 h. The reaction mixture was allowed to cool overnight and the precipitate was filtered off, washed with cold MeOH (3×50 mL) to give ethyl 3-amino-4-cyano-5-(methylsulfanyl)thiophene-2-carboxylate (52.4 g, 99%). LCMS: (FA) ES+ 275.

Step 2: Ethyl 4-cyano-3-iodo-5-(methylsulfanyl)thiophene-2-carboxylate

Ethyl 3-amino-4-cyano-5-(methylsulfanyl)thiophene-2-carboxylate (10 g, 41.3 mmol) was dissolved in acetonitrile (50 mL) under atmosphere of argon. Diiodomethane (11.6 mL, 0.144 mol) was added and the mixture was heated at 40° C. Isoamyl nitrite (12.1g, 0.103 mol) was added and the reaction was allowed to cool to room temperature and stirred for 2 hours. Mixture was cooled down at 0° C., diluted with hexane (50 mL) and the precipitate was filtered off, washed with 10:1 hexane-acetonitrile mixture (10 mL), 3:1 hexane-ether (10 mL) and hexane (10 mL). The precipitate was dried to afford ethyl 4-cyano-3-iodo-5-(methylsulfanyl)thiophene-2-carboxylate (6.90 g, 45%). LCMS: (FA) ES+ 354. $^1$H NMR (400 MHz, $d_1$-chloroform) δ: 4.38 (q, 2H), 2.70 (s, 3H), 1.40 (t, 3H).

Step 3: Ethyl 4-cyano-3-iodo-5-(methylsulfonyl) thiophene-2-carboxylate

Ethyl 4-cyano-3-iodo-5-(methylsulfanyl)thiophene-2-carboxylate (7.2 g, 20.4 mmol) was dissolved in DCM (200 mL) and THF (100 mL) and m-CPBA (9.14 g, 40.8 mmol) was added. The reaction mixture was stirred at rt overnight. Sodium sulfite (5.14 g, 40.8 mmol) was added, stirred for 10 minutes followed by addition of potassium carbonate (8.45, 61.2 mmol). The suspension was stirred at rt for 1 hour and filtered through celite, washed with DCM and the solvent was evaporated to afford ethyl 3-iodo-4-cyano-5-(methylsulfonyl)thiophene-2-carboxylate (6.80 g, 78%). LCMS: (FA) ES+ 386. $^1$H NMR (400 MHz, $d_1$-chloroform) δ: 4.45 (q, 2H), 3.38 (s, 3H), 1.43 (t, 3H).

Step 4: Ethyl 4-cyano-5-(2-(fluoromethyl)morpholino)-3-iodothiophene-2-carboxylate A mixture of ethyl 4-cyano-3-iodo-5-(methylsulfonyl)thiophene-2-carboxylate (718 mg, 0.00186 mol), 2-(fluoromethyl)morpholine hydrochloride (348 mg, 0.00224 mol) and TEA (1.0 mL, 0.0072 mol) in THF (7.1 mL, 0.088 mol) was flushed with argon and then heated at 90° C. overnight. The reaction mixture was concentrated and purified by column chromatography to give ethyl 4-cyano-5-(2-(fluoromethyl)morpholino)-3-iodothiophene-2-carboxylate (288 mg, 36.4%). LCMS: (FA) ES+ 425, $^1$H NMR (400 MHz, $d_1$-chloroform) δ: 4.57 (d, 1H), 4.46 (d, 1H), 4.34 (q, 2H), 4.12-4.05 (m, 1H), 4.02-3.77 (m, 4H), 3.34-3.25 (m, 1H), 3.22-3.14 (m, 1H), 1.37 (t, 3H).

Step 5: ethyl 4-cyano-3-(2,4-dichlorophenyl)-5-(2-(fluoromethyl)morpholino)thiophene-2-carboxylate A mixture of ethyl 4-cyano-5-(2-(fluoromethyl)morpholino)-3-iodothiophene-2-carboxylate (288 mg, 0.000679 mol), 2,4-dichlorophenylboronic acid (262 mg, 0.00137 mol), tetrakis(triphenylphosphine)palladium(0) (51 mg, 0.000044 mol) and sodium carbonate (220 mg, 0.0021 mol) in water (3 mL, 0.1 mol) and 1,2-dimethoxyethane (10 mL, 0.1 mol) was flushed with argon and then irradiated in microwave at 140° C. for 12 min. The reaction mixture was filtered and concentrated in vacuum to afford ethyl 4-cyano-3-(2,4-dichlorophenyl)-5-(2-(fluoromethyl)morpholino)thiophene-2-carboxylate (300 mg, 99%). LCMS: (FA) ES+ 443.15.

Step 6: 4-cyano-3-(2,4-dichlorophenyl)-5-(2-(fluoromethyl)morpholino)thiophene-2-carboxylic acid A mixture of ethyl 4-cyano-3-(2,4-dichlorophenyl)-5-(2-(fluoromethyl)morpholino)thiophene-2-carboxylate (300 mg, 0.00054 mol), Sodium hydroxide (0.12 g, 0.0030 mol) in EtOH (10.0 mL, 0.171 mol) and water (3.0 mL, 0.17 mol) was stirred at rt until completion by LCMS. The mixture was concentrated and the residue was acidified by 1N HCl. The precipitate was collected and dried in air and vacuum to afford 4-cyano-3-(2,4-dichlorophenyl)-5-(2-(fluoromethyl)morpholino)thiophene-2-carboxylic acid (225 mg, 99%). LCMS: (FA) ES+ 415, ES– 413.

Step 7: 4-cyano-3-(2,4-dichlorophenyl)-5-(2-(fluoromethyl)morpholino)thiophene-2-carboxamide A mixture of 4-cyano-3-(2,4-dichlorophenyl)-5-(2-(fluoromethyl)morpholino)thiophene-2-carboxylic acid (68.0 mg, 0.000164 mol), 33% ammonium hydroxide (33:67, ammonia:water, 0.1416 mL), EDCI (94.2 mg, 0.000491 mol) and 1-HOBT (66.4 mg, 0.000491 mol) in DCM (7 mL, 0.1 mol) was stirred at rt overnight. The reaction mixture was diluted with DCM and washed with water, the organic layer was dried and purified by column chloromatography to afford 4-cyano-3-(2,4-dichlorophenyl)-5-(2-(fluoromethyl)morpholino)thiophene-2-carboxamide (38 mg, 56%). LCMS: (FA) ES+ 414, ES– 412; $^1$H NMR (400 MHz, $d_1$-chloroform) δ: 7.59 (d, 1H), 7.42 (dd, 1H), 7.31 (d, 1H), 6.00 (s, 1H), 4.50 (dd, 2H), 4.12-4.08 (m, 2H), 4.00-3.78 (m, 4H), 3.36-3.25 (m, 1H), 3.22-3.15 (m, 1H)

Step 8: 4-(2,4-dichlorophenyl)-2-(2-(fluoromethyl)morpholino)-5-(4H-1,2,4-triazol-3-yl)thiophene-3-carbonitrile A solution of 4-cyano-3-(2,4-dichlorophenyl)-5-[2-(fluoromethyl)morpholin-4-yl]thiophene-2-carboxamide (38 mg, 0.000092 mol) in 1,1-dimethoxy-N,N-dimethylmethanamine (2.0 mL, 0.015 mol) was irradiated in microwave at 160° C. for 40 min. The solvent was removed and the residue was dissolved in AcOH (1.6 mL, 0.028 mol). Hydrazine monohydrate (0.3 mL, 0.006 mol) was added and the mixture was irradiated in microwave at 120° C. for 10 min. The reaction mixture was concentrated and the residue was treated with water, the solid was collected, dried to afford 4-(2,4-dichlorophenyl)-2-(2-(fluoromethyl)morpholino)-5-(4H-1,2,4-triazol-3-yl)thiophene-3-carbonitrile (23.5 mg, 60%). LCMS: (FA) ES+ 438, ES– 436; $^1$H NMR (400 MHz, $d_6$-DMSO) δ: 8.01 (s, 1H), 7.57 (d, 1H), 7.39 (dd, 1H), 7.32 d, 1H), 4.59 (t, 1H), 4.47 (t, 1H), 4.08-4.01 (m, 1H), 4.00-3.81 (m, 5H), 3.32-3.20 (m, 1H), 3.18-3.09 (m, 1H).

Compounds in the following table were prepared from the appropriate starting materials in a method analogous to that of Example 2:

| | |
|---|---|
| 3 | LCMS: (FA) ES+ 434. |
| 7 | LCMS: (FA) ES+ 438. |
| 9 | LCMS: (FA) ES+ 434. |
| 14 | LCMS: (FA) ES+ 434. |
| 15 | LCMS: (FA) ES+ 420. |
| 17 | LCMS: (FA) ES+ 368. |
| 32 | LCMS: (FA) ES+ 438. |
| 33 | LCMS: (FA) ES+ 388. |
| 35 | LCMS: (FA) ES+ 434. |

EXAMPLE 3

Synthesis of 4-(2,4-dichlorophenyl)-2-[2-(hydroxymethyl)morpholin-4-yl]-5-(4H-1,2,4-triazol-3-yl)thiophene-3-carbonitrile (Compound I-27)

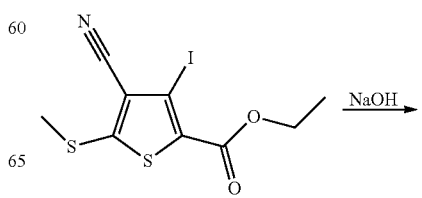

Step 1: 4-cyano-3-iodo-5-(methylsulfanyl)thiophene-2-carboxylic acid

To a solution of ethyl 4-cyano-3-iodo-5-(methylsulfanyl) thiophene-2-carboxylate (3.40 g, 10 mmol) in tetrahydrofuran (80 mL) and water (16 mL) was added a solution of 1.00M sodium hydroxide in water (30 mL). The solution was allowed to stir overnight. The reaction was quenched with a solution of 1N hydrogen chloride in water (50 mL) and diluted with water (400 mL). The resultant precipitate was filtered, washed with water (2×100 mL) and dried in a vacuum oven to give 4-cyano-3-iodo-5-(methylsulfanyl) thiophene-2-carboxylic acid (2.6 g, 79%) as a white solid. LCMS: (FA) ES+ 326. $^1$H NMR (400 MHz, d$_6$-DMSO) δ: 14.1-13.8 (bs, 1H), 2.75 (s, 3H).

Step 2: 4-cyano-3-iodo-5-(methylsulfanyl)thiophene-2-carboxamide

To a suspension of 4-cyano-3-iodo-5-(methylsulfanyl) thiophene-2-carboxylic acid (2.85 g, 7.93 mmol) in methylene chloride (30 mL), were added N-(3-dimethylaminopropyl)-N'-ethylcarbodiimide hydrochloride (3.28 g, 17.1 mmol) and 1-hydroxybenzotriazole (2.27 g, 16.8 mmol). The reaction mixture was stirred at room temperature for two hours and ammonium hydroxide (15.4 mL) was added and the biphasic mixture was stirred at room temperature for two hours. Water (100 mL), methanol (50 mL), methylene chloride (200 mL) was added. The organic layer was removed. The aqueous layer was extracted five times with a solution of 20% methanol in methylene chloride (100 mL). The combined organic extracts were dried over anhydrous magnesium sulfate, filtered and concentrated to the title compound as dark red oil (1.47 g, 57%). LCMS: (FA) ES+ 325.

Step 3: 4-cyano-3-iodo-5-(methylsulfonyl)thiophene-2-carboxamide

To a solution of 4-cyano-3-iodo-5-(methylsulfanyl) thiophene-2-carboxamide (1.46 g, 4.50 mmol) in methylene chloride (60 mL), tetrahydrofuran (20 mL), N,N-dimethylformamide (20 mL), m-chloroperbenzoic acid (5.05 g, 22.5 mmol) was added and the mixture was stirred at room temperature overnight. The methylene chloride was removed in vacuo. The remaining residue was diluted with ethyl acetate (200 mL) and washed three times with a solution of 1.00M sodium hydroxide in water (50 mL). The organic phase was removed and the aqueous phase was extracted five times with ethyl acetate (100 mL). The combined organic extracts were washed twice with a solution of 1.00M sodium hydroxide in water (50 mL). The organic extracts were concentrated in vacuo. The residue was suspended in water (100 mL) and a precipitate formed. The precipitate was filtered, washed with water (40 mL), hexanes (100 mL), and dried in a vacuum oven to give the title compound as a white solid (1.00 g, 62%). LCMS: (FA) ES+ 357. $^1$H NMR (400 MHz, d$_6$-DMSO) δ: 8.16 (s, 2H), 3.56 (s, 3H).

Step 4: 4-cyano-3-(2,4-dichlorophenyl)-5-(methylsulfonyl)thiophene-2-carboxamide 4-cyano-3-iodo-5-(methylsulfonyl)thiophene-2-carboxamide (0.500 g, 1.40 mmol), bis(dibenzylideneacetone)palladium (0.040 g, 0.0700 mmol), bis(2-diphenylphosphinophenyl)ether (0.057 g, 0.100 mmol), and potassium phosphate (0.596 g, 2.81 mmol) were suspended in 1,2-dimethoxyethane (10.0 mL) and N,N-dimethylacetamide (5 mL). The suspension was flushed with argon and the reaction mixture was irradiated in microwave at 150° C. (300 watts) for three hours. The reaction mixture was concentrated in vacuo and column chromatography was performed to yield the title compound (0.080 g, 14%) as beige foam. $^1$H NMR (400 MHz, d$_4$-methanol) δ: 7.71-7.69 (m, 1H), 7.52-7.50 (m, 2 H), 3.46 (s, 3H).

Step 5: 4-cyano-3-(2,4-dichlorophenyl)-5-[2-(hydroxymethyl)morpholin-4-yl]thiophene-2-carboxamide 4-cyano-3-(2,4-dichlorophenyl)-5-(methylsulfonyl) thiophene-2-carboxamide (0.026 g, 0.069 mmol) was dissolved in 2-hydroxymethylmorpholine (0.300 g, 2.56 mmol) and the solution was heated at 60° C. overnight. The residue was concentrated in vacuo and column chromatography was performed and yielded 4-cyano-3-(2,4-dichlorophenyl)-5-[2-(hydroxymethyl)morpholin-4-yl]thiophene-2-carboxamide (0.020 g, 66%) as a white solid. LCMS: (FA) ES+ 412. $^1$H NMR (400 MHz, d$_4$-methanol) δ: 7.76 (s, 1H), 7.49 (d, 1H), 7.40 (d, 1H), 4.08-3.92 (m, 3H), 3.84-3.72 (m, 2H), 3.69-3.59 (m, 2H), 3.15-3.08 (m, 2H).

Step 6: Synthesis of 4-(2,4-dichlorophenyl)-2-[2-(hydroxymethyl)morpholin-4-yl]-5-(4H-1,2,4-triazol-3-yl)thiophene-3-carbonitrile A mixture of 4-cyano-3-(2,4-dichlorophenyl)-5-[2-(hydroxymethyl)morpholin-4-yl]thiophene-2-carboxamide (115 mg, 0.279 mmol) in 1,1-dimethoxy-N,N-dimethyl-methanamine (3.44 mL, 0.025 mol) was flushed with argon and then irradiated in microwave at 160° C. for 60 min. The reaction mixture was concentrated to give 4-cyano-3-(2,4-dichlorophenyl)-N-[(1E)-(dimethylamino)methylene]-5-[2-(hydroxymethyl)morpholin-4-yl]thiophene-2-carboxamide (130 mg, 99%). LCMS: (FA) ES+ 467. To the above intermediate in AcOH (4.3 mL, 0.076 mol) was added hydrazine hydrate (100 mg, 0.003 mol). The mixture was flushed with argon and then irradiated in microwave at 120° C. for 20 min. The mixture was concentrated to remove the solvent. The residue was purified using ISCO chromatography on silica gel, elution 1:1 hexane-ethyl acetate to ethylacetate to afford 4-(2,4-dichlorophenyl)-2-[2-(hydroxymethyl)morpholin-4-yl]-5-(4H-1,2,4-triazol-3-yl)thiophene-3-carbonitrile (90 mg, 70%). LCMS: (FA) ES+ 436, $^1$H NMR (400 MHz, d$_4$-methanol) δ: 8.28 (s, 1H), 7.55 (d, 1H), 7.41 (dd, 1H), 7.34 (d, 1H), 4.12-3.72 (m, 5H), 3.68-3.61 (m, 2H), 3.30-3.20 (m, 1H), 3.12-3.02 (m, 1H).

Compounds in the following table were prepared from the appropriate starting materials in a method analogous to that of Example 3:

| | |
|---|---|
| 20 | LCMS: (FA) ES+ 436. |
| 24 | LCMS: (FA) ES+ 492. |
| 28 | LCMS: (FA) ES+ 436. |
| 31 | LCMS: (FA) ES+ 478. |
| 36 | LCMS: (FA) ES+ 450. |

EXAMPLE 4

Synthesis of 4-(2,4-dichlorophenyl)-5-(1H-imidazol-2-yl)-2-morpholine-3-carbonitrile (Compound I-22)

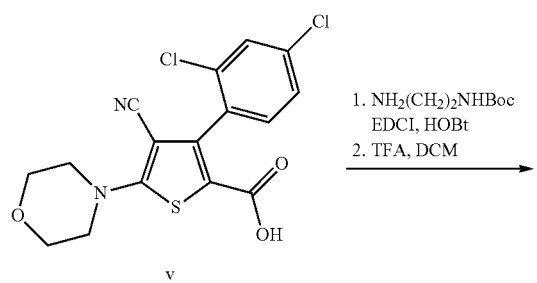

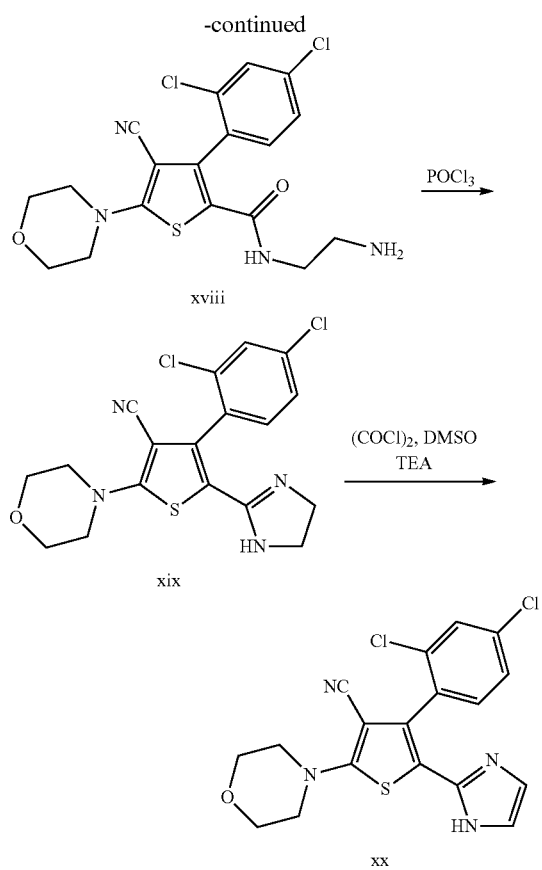

Step 1: N-(2-aminoethyl)-4-cyano-3-(2,4-dichlorophenyl)-5-morpholin-4-ylthiophene-2-carboxamide To a solution of 4-cyano-3-(2,4-dichlorophenyl)-5-morpholin-4-ylthiophene-2-carboxylic acid (3.10 g, 8.2 mmol) and N-(2-aminoethyl)(tert-butoxy)carboxamide (1.98 gr, 12.3 mmol) in methylene chloride (60 mL) was added N-(3-dimethylaminopropyl)-N'-ethylcarbodiimide hydrochloride (3.15 gr, 16.4 mmol) and 1-hydroxybenzotriazole (2.22 gr, 16.4 mmol) at room temperature. The solution was allowed to stir overnight. The reaction was diluted with methylene chloride and water. The layers were separated and the organic layer was dried over anhydrous sodium sulfate, filtered and concentrated in vacuo. The residue was purified by column chromatography to give the intermediate boc-protected product as a yellow solid. The material was dissolved in dioxane (4 mL) and a solution 4N HCl in dioxane (9 mL) was added. The solution was stirred at room temperature for 30 minutes. The solvents were evaporated and the residue was dried under vacuum overnight. The product was converted to the free base by suspension in methylene chloride followed by addition of sodium carbonate solution. The layers were separated and the aqueous layer was extracted twice with methylene chloride. The combined organic extracts were dried over anhydrous sodium sulfate, filtered and concentrated in vacuo to afford the product as a free base (2.55 gr, 67%). LCMS: (FA) ES+ 463. $^1$H NMR (400 MHz, d$_1$-chloroform) δ: 7.59-7.55 (m, 1H), 7.43-7.30 (m, 2H), 3.90-3.82 (m, 4H), 3.64-3.57 (m, 4H), 3.53-2.85 (m, 4H).

Step 2: 4-(2,4-dichlorophenyl)-5-(4,5-dihydro-1H-imidazol-2-yl)-2-morpholin-4-ylthiophene-3-carbonitrile To a suspension of N-(2-aminoethyl)-4-cyano-3-(2,4-dichlorophenyl)-5-morpholin-4-ylthiophene-2-carboxamide (2.50 g, 5.90 mmol) in toluene (20 mL) was added phosphoryl chloride (4.70 mL, 50.0 mmol) and the mixture was stirred under microwave irradiation at 120° C. for 25 minutes. The reaction mixture was evaporated and the residue was suspended in methylene chloride and then quenched with ice water. The aqueous layer was basified by addition of KOH, the layers were separated and the aqueous layer was extracted again with methylene chloride. The organic layers were combined and washed with brine, dried over anhydrous sodium sulfate, filtered and concentrated in vacuo to afford the crude product (2.3 gr, 77%). LCMS: (FA) ES+ 408. $^1$H NMR (400 MHz, d$_6$-DMSO) δ: 7.78-7.75 (m, 1H), 7.52-7.49 (m, 2H), 3.79-3.73 (m, 4H), 3.63-3.55 (m, 2H), 3.54-3.48 (m, 4H), 3.20-3.11 (m, 2H).

Step 3: 4-(2,4-dichlorophenyl)-5-(1H-imidazol-2-yl)-2-morpholine-3-carbonitrile

To a solution of dimethyl sulfoxide (2.50 mL, 35.3 mmol) in methylene chloride (100 mL) at −78° C. under an atmosphere of argon was added oxalyl chloride (2.98 mL, 35.3 mmol). The solution was stirred for 40 minutes, then a solution of 4-(2,4-dichlorophenyl)-5-(4,5-dihydro-1H-imidazol-2-yl)-2-morpholin-4-ylthiophene-3-carbonitrile (1.45 g, 3.03 mmol) in methylene chloride (40 mL) was added dropwise and the reaction was stirred for 1 hour at −78° C. Triethylamine (14.0 mL, 100 mmol) was added and stirring was continued at −78° C. for 1 hour. Then added 33% ammonium hydroxide (10 mL), and the mixture was allowed to warm to room temperature. Added sodium bicarbonate solution, the layers were separated and the organic extract was dried over anhydrous sodium sulfate, filtered and concentrated in vacuo to afford the crude product. The residue was purified by column chromatography to give the product as a yellow solid (0.90 gr, 75%) which was dried overnight at 39° C. in a vacuum oven LCMS: (FA) ES+ 406. $^1$H NMR (400 MHz, d$_1$-chloroform) δ: 8.20-8.11 (s, 1H), 7.65-7.62 (m, 1H), 7.45-7.41 (m, 1H), 7.37-7.33 (m, 1H), 7.03-7.00 (m, 1H), 6.85-6.81 (m, 1H), 3.90-3.84 (m, 4H), 3.62-3.55 (m, 4H).

Compounds in the following table were prepared from the appropriate starting materials in a method analogous to that of Example 4:

| 16 | LCMS: (FA) ES+ 401. |
| 30 | LCMS: (FA) ES+ 437. |

EXAMPLE 5

Synthesis of 4-(2,4-dichlorophenyl)-5-(4-methyl-1H-imidazol-2-yl)-2-morpholinothiophene-3-carbonitrile (Compound I-13)

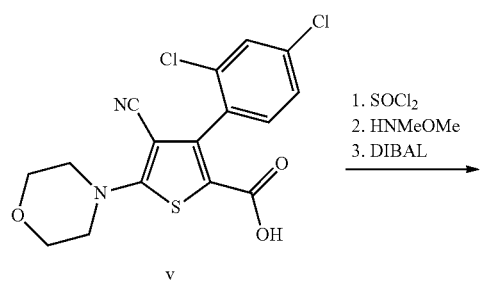

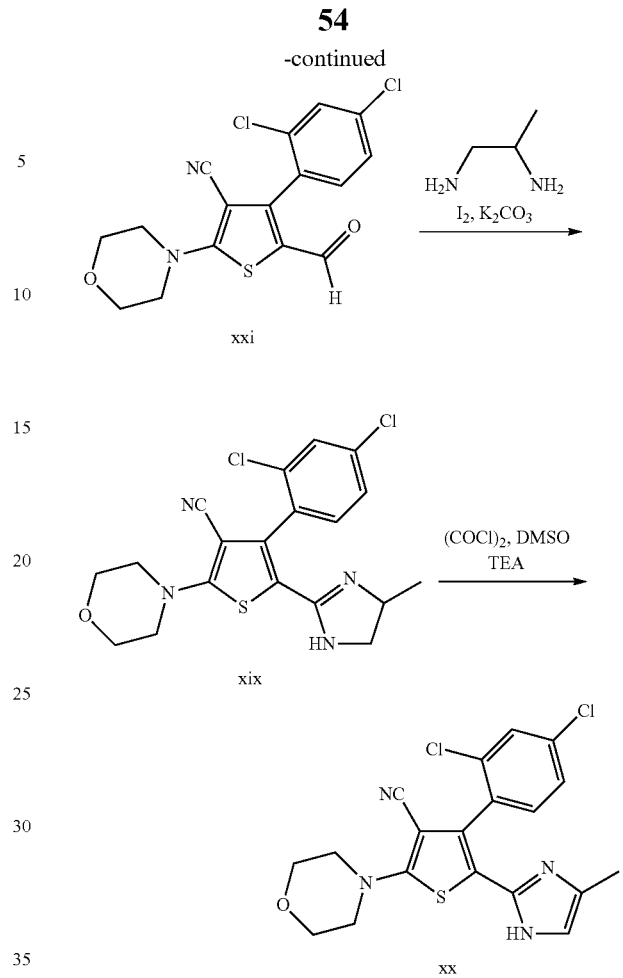

Step 1: 5-acetyl-4-(2,4-dichlorophenyl)-2-morpholinothiophene-3-carbonitrile

A mixture of 4-cyano-3-(2,4-dichlorophenyl)-5-morpholinothiophene-2-carboxylic acid (508.0 mg, 0.001326 mol) in thionyl chloride (1.7 mL, 0.024 mol) and toluene (10 mL, 0.098 mol) was heated at 80° C. for 1 h. The mixture was evaporated in vaccum and the residue was coevaporated with toluene for 3 times to afford acid chloride as dark brown oil. This oil was dissolved in DCM (3 mL, 0.05 mol) and added to TEA (1.3 mL, 0.0093 mol) and N,O-dimethylhydroxylamine hydrochloride (282 mg, 0.00289 mol) in DCM (9 mL, 0.1 mol) at 0° C. The mixture was stirred for 1 h at the same temperature. The reaction mixture was washed with water and dried over sodium sulfate. The organic layer was evaporated to afford 4-cyano-3-(2,4-dichlorophenyl)-N-methoxy-N-methyl-5-morpholinothiophene-2-carboxamide. To the above intermediate (207.0 mg, 0.0004856 mol) in THF (21 mL, 0.26 mol) was added diisobutylaluminum hydride in hexane solution (1M, 0.1 ml, 0.0019 mol) at −78° C. and the mixture was stirred at the same temperature for 30 min. The reaction mixture was raised to 0° C. for 5 min and cooled to −78° C. again. Quenched by MeOH and water and then purified by column chromatography to afford 4-(2,4-dichlorophenyl)-5-formyl-2-morpholinothiophene-3-carbonitrile (115 mg, 65%). LCMS: (FA) ES+ 367. 1H NMR (400 MHz, d$_1$-chloroform) δ: 9.23 (s, 1H), 7.55 (d, 1H), 7.37 (dd, 1H), 7.30 (d, 1H), 3.88-3.84 (m, 4H), 3.74-3.70 (m, 4H), 1.90 (s, 3H).

Step 2: 4-(2,4-dichlorophenyl)-5-(4-methyl-4,5-dihydro-1H-imidazol-2-yl)-2-morpholinothiophene-3-carbonitrile To 4-(2,4-dichlorophenyl)-5-formyl-2-morpholin-4-ylthiophene-3-carbonitrile (52.0 mg, 0.000142 mol) in tert-butyl alcohol (0.75 g, 0.010 mol) was added 1,2-diaminopropane (12.9 mg, 0.000174 mol) and the mixture was stirred for 30 min. Iodine (51 mg, 0.00020 mol) and potassium carbonate (65.7 mg, 0.000475 mol) was added the mixture was stirred at 70° C. for 3 hr. The reaction mixture was quenched by saturated sodium bicarbonate solution and brine. The organic layer was collected and purified by column chromatography to afford 4-(2,4-dichlorophenyl)-5-(4-methyl-4,5-dihydro-1H-imidazol-2-yl)-2-morpholinothiophene-3-carbonitrile (19 mg, 32%). LCMS: (FA) ES+ 421. 1H NMR (400 MHz, $d_1$-chloroform) δ: 7.60 (s, 1H), 7.50-7.40 (m, 1H), 7.40-7.30 (m, 1H), 4.20-4.05 (m, 1H), 3.90-3.75 (m, 5H), 3.60-3.70 (m, 4H), 3.38-3.20 (m, 1H), 1.25 (s, 3H).

Step 3: 4-(2,4-dichlorophenyl)-5-(4-methyl-1H-imidazol-2-yl)-2-morpholinothiophene-3-carbonitrile To DMSO (32.0 uL, 0.000451 mol) in DCM (3 mL, 0.05 mol) at −78° C. was added oxalyl chloride (38.2 uL, 0.000451 mol) and the mixture was stirred for 30 min. 4-(2,4-dichlorophenyl)-5-(4-methyl-4,5-dihydro-1H-imidazol-2-yl)-2-morpholinothiophene-3-carbonitrile (19 mg, 0.000045 mol) in DCM (1.5 mL, 0.023 mol) was added. After 1 h, TEA (0.188 mL, 0.00135 mol) was added and the mixture was stirred for another 30 min. 33% ammonium hydroxide (33:67, ammonia:Water, 0.117 mL) was added and the reaction mixture was warmed to room temperature. The mixture was purified by column chromatography to afford 4-(2,4-dichlorophenyl)-5-(4-methyl-1H-imidazol-2-yl)-2-morpholinothiophene-3-carbonitrile (4.04 mg, 21%). LCMS: (FA) ES+ 419.13, ES− 417.17. 1H NMR (400 MHz, $d_1$-chloroform) δ: 7.61 (d, 1H), 7.42 (dd, 1H), 7.34 (d, 1H), 6.61 (s, 1H), 3.88-3.84 (m, 4H), 3.62-3.57 (m, 4H), 2.21 (s, 3H).

Compounds in the following table were prepared from the appropriate starting materials in a method analogous to that of Example 5:

| 2 | LCMS: (FA) ES+ 473. |
|---|---|

EXAMPLE 6

Synthesis of 4-(2,4-dichlorophenyl)-5-(1H-imidazol-5-yl)-2-morpholinothiophene-3-carbonitrile (Compound I-19)

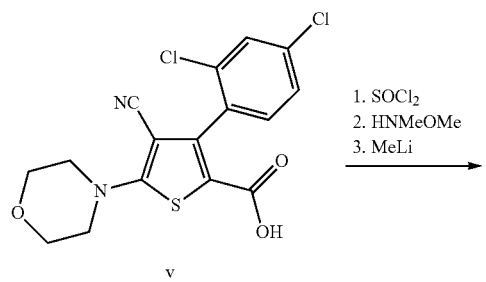

1. SOCl₂
2. HNMeOMe
3. MeLi

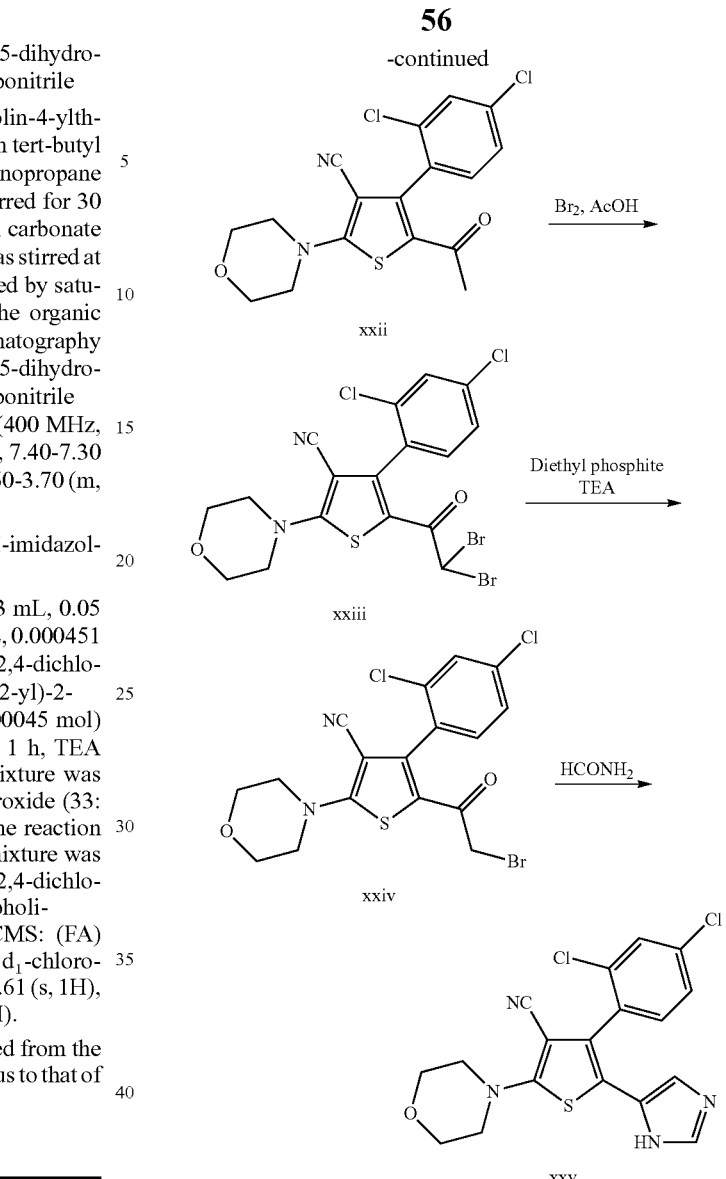

Step 1: 5-acetyl-4-(2,4-dichlorophenyl)-2-morpholinothiophene-3-carbonitrile

A mixture of 4-cyano-3-(2,4-dichlorophenyl)-5-morpholinothiophene-2-carboxylic acid (508.0 mg, 0.001326 mol) in thionyl chloride (1.7 mL, 0.024 mol) and toluene (10 mL, 0.098 mol) was heated at 80° C. for 1 h. The mixture was evaporated in vaccum and the residue was coevaporated with toluene for 3 times to afford acid chloride as dark brown oil. This oil was dissolved in DCM (3 mL, 0.05 mol) and added to TEA (1.3 mL, 0.0093 mol) and N,O-dimethylhydroxylamine hydrochloride (282 mg, 0.00289 mol) in DCM (9 mL, 0.1 mol) at 0° C. The mixture was stirred for 1 h at the same temperature. The reaction mixture was washed with water and dried over sodium sulfate. The organic layer was evaporated to afford 4-cyano-3-(2,4-dichlorophenyl)-N-methoxy-N-methyl-5-morpholinothiophene-2-carboxamide. To the above intermediate in THF (50 mL, 0.6 mol) was added methyllithium in diethyl ether solution (1.4M) (1.7 ml, 0.00244 mol) at −78° C. After about 15 min, the reaction mixture was quenched by ammonium chloride solution and extracted with ethyl acetate. The organic layer was washed with brine and purified by column chromatography to afford 5-acetyl-4-(2,4-dichlorophenyl)-2-morpholinothiophene-3-carbonitrile (397 mg, 78%). LCMS: (FA) ES+ 381.05. $^1$H NMR (400 MHz, d$_1$-chloroform) δ: 7.60 (d, 1H), 7.40 (dd, 1H), 7.28 (dd, 1H), 3.90-3.83 (m, 4H), 3.71-3.64 (m, 4H), 1.90 (s, 3H).

Step 2: 5-(2,2-dibromoacetyl)-4-(2,4-dichlorophenyl)-2-morpholinothiophene-3-carbonitrile A solution of 5-acetyl-4-(2,4-dichlorophenyl)-2-morpholin-4-ylthiophene-3-carbonitrile (50.0 mg, 0.000131 mol) and bromine (42 mg, 0.00026 mol) in AcOH (1.0 mL, 0.018 mol) was flushed with argon and then irradiated in microwave at 120° C. for 5 min. The reaction mixture was concentrated and the residue was suspended in water. The solid was collected to gave 5-(2,2-dibromoacetyl)-4-(2,4-dichlorophenyl)-2-morpholinothiophene-3-carbonitrile (46.9 mg, 66%). LCMS: (FA) ES+ 538.87; $^1$H NMR (400 MHz, d$_1$-chloroform) δ: 7.82 (d, 1H), 7.45 (dd, 1H), 7.33 (d, 1H), 5.78 (s, 1H), 4.00-3.85 (m, 4H), 3.80-3.70 (m, 4H).

Step 3: 5-(2-bromoacetyl)-4-(2,4-dichlorophenyl)-2-morpholinothiophene-3-carbonitrile To a mixture of 5-(dibromoacetyl)-4-(2,4-dichlorophenyl)-2-morpholin-4-ylthiophene-3-carbonitrile (46.9 mg, 0.0000870 mol) in THF (0.78 mL, 0.0096 mol) was added diethyl phosphite (13.7 uL, 0.000107 mol) and TEA (14.9 uL, 0.000107 mol) at 0° C. After addition, the mixture was warmed to rt after 20 min. The reaction mixture was evaporated and the residue was suspended in ice/water. The solid was filtered and purified by column chromatography to afford 5-(2-bromoacetyl)-4-(2,4-dichlorophenyl)-2-morpholinothiophene-3-carbonitrile (12 mg, 30%). LCMS: (FA) ES+ 460.88; $^1$H NMR (400 MHz, d$_1$-chloroform) δ: 7.59 (d, 1H), 7.42 (dd, 1H), 7.33 (d, 1H), 3.90-3.85 (m, 4H), 3.75-3.69 (m, 5H), 3.62 (d, 1H).

Step 4: 4-(2,4-dichlorophenyl)-5-(1H-imidazol-5-yl)-2-morpholinothiophene-3-carbonitrile 5-(Bromoacetyl)-4-(2,4-dichlorophenyl)-2-morpholin-4-ylthiophene-3-carbonitrile (50 mg, 0.0001 mol) in formamide (1.3 mL, 0.033 mol) was flushed with argon and then irradiated in microwave at 180° C. for 30 min. The reaction mixture was concentrated and the residue was purified by preparative HPLC to afford 4-(2,4-dichlorophenyl)-5-(1H-imidazol-5-yl)-2-morpholinothiophene-3-carbonitrile (2.8 mg, 6%). LCMS: (FA) ES+ 405.18, ES− 403.27; $^1$H NMR (400 MHz, d$_4$-methanol) δ: 7.66 (d, 1H), 7.60 (s, 1H), 7.46 (dd, 1H), 7.35 (d, 1H), 6.27 (s, 1H), 3.89-3.40 (m, 4H), 3.55-3.49 (m, 4H).

EXAMPLE 7

Synthesis of 4-(2,4-dichlorophenyl)-2-morpholino-5-(1H-pyrazol-5-yl)thiophene-3-carbonitrile (Compound I-21)

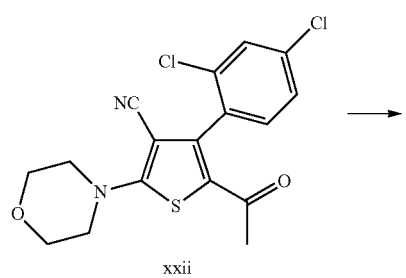

xxii

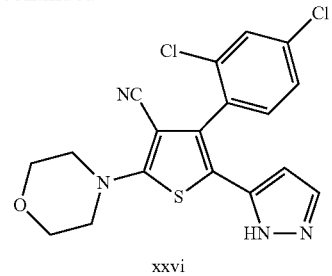

xxvi

Step 1: 4-(2,4-dichlorophenyl)-2-morpholino-5-(1H-pyrazol-5-yl)thiophene-3-carbonitrile A solution of 5-acetyl-4-(2,4-dichlorophenyl)-2-morpholin-4-ylthiophene-3-carbonitrile (52.3 mg, 0.000137 mol) in 1,1-dimethoxy-N,N-dimethylmethanamine (1.0 mL, 0.0075 mol) was flushed with argon and irradiated in microwave at 160° C. for 30 min. The reaction mixture was evaporated to dryness to give 4-(2,4-dichlorophenyl)-5-(3-(dimethylamino)acryloyl)-2-morpholinothiophene-3-carbonitrile as an intermediate. The above intermediate and hydrazine hydrate (30 mg, 0.0006 mol) in AcOH (1.5 mL, 0.026 mol) was irradiated in microwave at 120° C. for 15 min. The reaction mixture was evaporated and the residue was purified by column chromatography to afford 4-(2,4-dichlorophenyl)-2-morpholino-5-(1H-pyrazol-5-yl)thiophene-3-carbonitrile (19.5 mg, 84%). LCMS: (FA) ES+ 405.06, ES− 403.23; $^1$H NMR (400 MHz, d$_4$-methanol) δ: 7.65 (d, 1H), 7.45 (m, 2H), 7.33 (d, 1H), 5.48 (s, 1H), 5.45 (br, 1H), 3.85 (m, 4H), 3.54 (m, 4H).

Compounds in the following table were prepared from the appropriate starting materials in a method analogous to that of Example 7:

| 29 | LCMS: (FA) ES+ 419. |

EXAMPLE 8

Synthesis of 4-(2,4-dichlorophenyl)-2-morpholino-5-(1H-tetrazol-5-yl)thiophene-3-carbonitrile (Compound I-23)

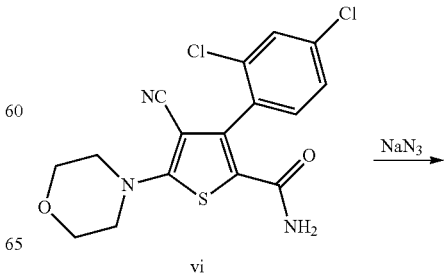

vi

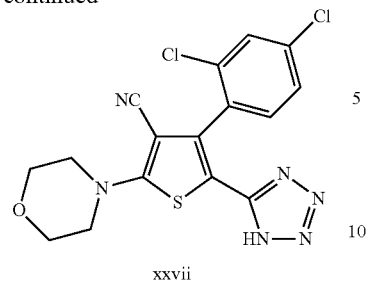

xxvii

Step 1: 4-(2,4-dichlorophenyl)-2-morpholino-5-(1H-tetra-zol-5-yl)thiophene-3-carbonitrile To a mixture of sodium azide (34.01 mg, 0.0005232 mol) in ACN (0.3 mL, 0.005 mol) was added silicon(IV) chloride (0.105 mmol, 0.000105 mol) in DCM (0.1 mL, 0.002 mol) and the mixture was stirred for 30 min. 4-cyano-3-(2,4-dichlorophenyl)-5-morpholinothiophene-2-carboxamide (20.0 mg, 0.0000523 mol) was added to the above mixture, followed by sodium azide (0.0340 g, 0.000523 mol) and silicon(IV) chloride (0.16 mmol, 0.00016 mol) in DCM (0.16 mL, 0.0025 mol) and the mixture was irradiated in microwave at 160° C. for 30 min. The reaction was evaporated and purified by column chromatography to afford 4-(2,4-dichlorophenyl)-2-morpholino-5-(1H-tetrazol-5-yl)thiophene-3-carbonitrile (11.6 mg, 54.4%). LCMS: (FA) ES+ 407.09, ES− 405.20; $^1$H NMR (300 MHz, $d_1$-chloroform) δ: 7.60 (d, 1H), 7.42 (dd, 1H), 7.30 (d, 1H), 3.90-3.85 (m, 4H), 3.72-3.63 (m, 4H).

Compounds in the following table were prepared from the appropriate starting materials in a method analogous to that of Example 7:

| 6 | LCMS: (FA) ES+ 389.22. |
|---|---|

EXAMPLE 9

Synthesis of 4-(2,4-dichlorophenyl)-2-(3,6-dihydro-2H-pyran-4-yl)-5-(4H-1,2,4-triazol-3-yl)thiophene-3-carbonitrile (Compound I-34) and 4-(2,4-dichlorophenyl)-2-(tetrahydro-2H-pyran-4-yl)-5-(4H-1,2,4-triazol-3-yl)thiophene-3-carbonitrile (Compound I-5)

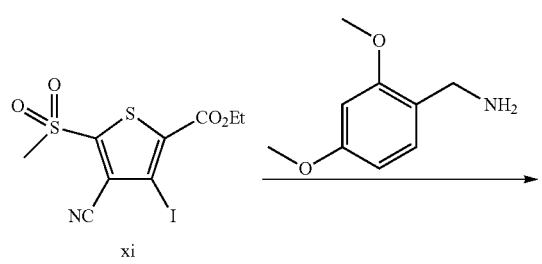

xi

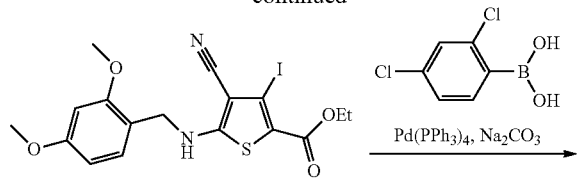

xxviii

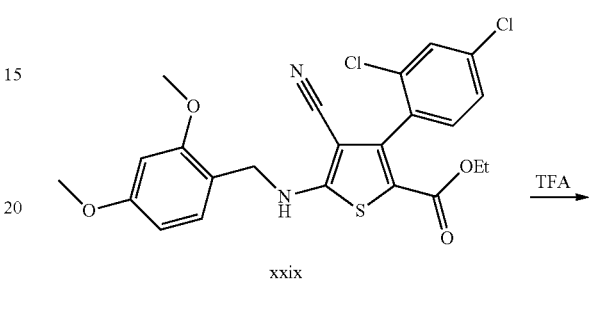

xxix

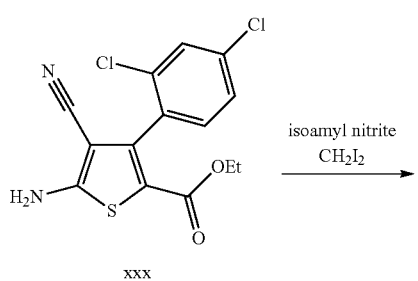

xxx

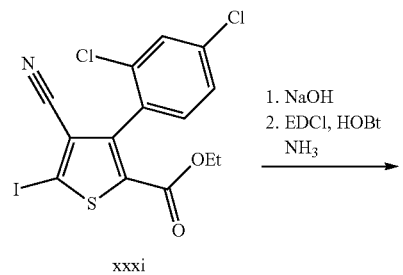

xxxi

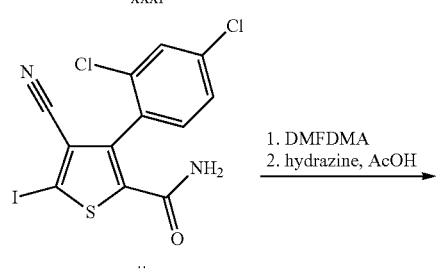

xxxii

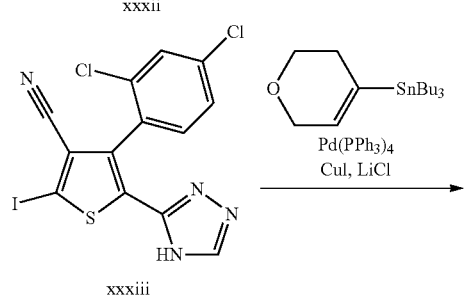

xxxiii

-continued

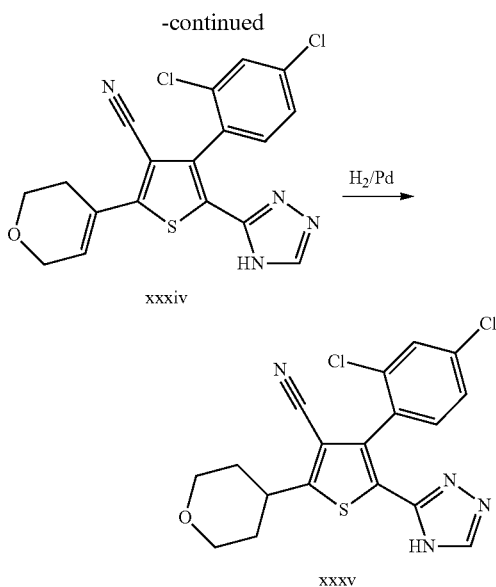

Step 1: Ethyl 4-cyano-5-[(2,4-dimethoxybenzyl)amino]-3-iodothiophene-2-carboxylate Ethyl 4-cyano-3-iodo-5-(methylsulfonyl)thiophene-2-carboxylate (5.60 g, 0.0145 mol) and 2,4-dimethoxybenzylamine (3.51 mL, 0.0234 mol) were combined in tetrahydrofuran (100 mL) and stirred at 60° C. for three days. The reaction was concentrated in vacuo, diluted with dichloromethane and hexanes and the resultant precipitate was filtered to yield the title compound (5.56, 81%) as a yellow solid. LCMS: (FA) ES+, 473. $^1$H NMR (400 MHz, d$_6$-DMSO) δ: 9.05 (s, 1H) 7.10 (d, 1H, J=8.57 Hz), 6.60-6.50 (m, 2H), 4.30 (s, 2H), 4.22-4.14 (m, 2H), 3.80 (s, 3H), 3.75 (s, 3H), 1.26-1.21 (m, 3H).

Step 2: Ethyl 4-cyano-3-(2,4-dichlorophenyl)-5-[(2,4-dimethoxybenzyl)amino]thiophene-2-carboxylate Ethyl 4-cyano-5-[(2,4-dimethoxybenzyl)amino]-3-iodothiophene-2-carboxylate (3.18 g, 0.00673 mol) 2,4-dichlorophenylboronic acid (2.72 g, 0.0143 mol), tetrakis(triphenylphosphine)palladium (0) (0.47 g, 0.00040 mol), and sodium carbonate (2.42 g, 0.0228 mol) were suspended in 1,2-dimethoxyethane (23.5 mL) and water (13.5 mL). The suspension was flushed with argon and the reaction mixture was irradiated in microwave at 140° C. (300 watts) for ten minutes. The reaction mixture was diluted with a saturated solution of sodium bicarbonate in water and extracted with ethyl acetate. The organic extracts were washed with brine, dried over anhydrous sodium sulfate, filtered and concentrated in vacuo. Column chromatography was performed to yield the title compound (2.92 g, 88%). LCMS: (FA) ES+, 491. $^1$H NMR (400 MHz, d$_6$-DMSO) δ: 9.05 (bs, 1H) 7.75 (d, 1H, J=2.00 Hz), 7.52-7.48 (m, 1H), 7.40 (d,1H, J=8.28 Hz), 7.19 (d, 1H, J=8.53 Hz), 6.62-6.53 (m, 2H), 4.35 (bs, 2H), 4.04-3.92 (m, 2H), 3.83 (s, 3H), 3.76 (s, 3H), 1.01-0.96 (m, 3H).

Step 3: Ethyl 5-amino-4-cyano-3-(2,4-dichlorophenyl)thiophene-2-carboxylate

Ethyl 4-cyano-3-(2,4-dichlorophenyl)-5-[(2,4-dimethoxybenzyl)amino]thiophene-2-carboxylate (4.70 g, 0.00956 mol) was dissolved in dichloromethane (100 mL). Trifluoroacetic acid (25 mL) was added and the solution was stirred at room temperature for ten minutes. The reaction was concentrated in vacuo, diluted with ethyl acetate and filtered. The filtrate was washed with saturated sodium bicarbonate and brine, dried over anhydrous sodium sulfate, filtered and concentrated in vacuo. Column chromatography was performed to yield the title compound (2.92 g, 90%) as a yellow solid. LCMS: (FA) ES+, 341. $^1$H NMR (400 MHz, d$_6$-DMSO) δ: 8.17 (s, 2H) 7.75 (d, 1H, J=2.00 Hz), 7.52-7.48 (m, 1H), 7.39 (d, 1H, J=8.28 Hz), 4.05-3.92 (m, 2H), 1.02-0.96 (m, 3H).

Step 4: Ethyl 4-cyano-3-(2,4-dichlorophenyl)-5-iodothiophene-2-carboxylate

To a suspension of ethyl 5-amino-4-cyano-3-(2,4-dichlorophenyl)thiophene-2-carboxylate (2.92 g, 0.00856 mol) in acetonitrile (10 mL) was added diiodomethane (2.41 mL, 0.0300 mol) under an atmosphere of argon and was heated at 38° C. Isoamyl nitrite (2.61 g, 0.0214 mol) was added dropwise and the reaction mixture was cooled to room temperature and stirred for one hour. The reaction was concentrated in vacuo and column chromatography was performed to yield the title compound (1.44 g, 37%) as an orange solid. $^1$H NMR (400 MHz, d$_1$-chloroform) δ: 7.53 (d, 1H, J=2.00 Hz), 7.38-7.34 (m, 1H), 7.21 (d,1H, J=8.28 Hz), 4.25-4.15 (m, 2H), 1.21-1.16 (m, 3H).

Step 5: 4-cyano-3-(2,4-dichlorophenyl)-5-iodothiophene-2-carboxylic acid

To a solution of ethyl 4-cyano-3-(2,4-dichlorophenyl)-5-iodothiophene-2-carboxylate (1.44 g, 0.00318 mol) in tetrahydrofuran (20 mL) and water (10 mL) was added a solution of 1.00M sodium hydroxide in water (16 mL). The solution was allowed to stir overnight. The reaction was quenched with a solution of 1N hydrogen chloride in water (18 mL) and extracted with ethyl acetate. The organic extracts were washed with brine, dried over anhydrous sodium sulfate, filtered and concentrated in vacuo to afford the crude title compound (1.50 g, 100%) used directly in the next reaction. LCMS: (FA) ES+, 378. $^1$H NMR (400 MHz, d$_6$-DMSO) δ: 7.68 (d, 1H, J=2.0 Hz), 7.46-7.34 (m, 2H).

Step 6: 4-cyano-3-(2,4-dichlorophenyl)-5-iodothiophene-2-carboxamide 4-cyano-3-(2,4-dichlorophenyl)-5-iodothiophene-2-carboxylic acid (1.30 g, 0.00306 mol) was dissolved in dichloromethane (30 mL). N-(3-dimethylaminopropyl)-N'-ethylcarbodiimide hydrochloride (1.27 g, 0.00661 mol) and 1-hydroxybenzotriazole (0.880 g, 0.00651 mol) were added to the solution and the reaction was stirred for thirty minutes. Ammonium hydroxide (5.97 mL, 0.153 mol) was added to the solution and the biphasic mixture was stirred for two hours. The reaction mixture was concentrated, diluted with water and extracted with ethyl acetate. The organic extract was dried over anhydrous magnesium sulfate, filtered and column chromatography was performed to yield the title compound (1.21 g, 89%). LCMS: (FA) ES+, 423. $^1$H NMR (400 MHz, d$_6$-DMSO) δ: 7.79 (d, 1H, J=2.0 Hz), 7.68 (bs, 1H), 7.57-7.45 (m, 2H), 7.30 (bs, 1H).

Step 7: 4-(2,4-dichlorophenyl)-2-iodo-5-(4H-1,2,4-triazol-3-yl)thiophene-3-carbonitrile A mixture of 4-cyano-3-(2,4-dichlorophenyl)-5-iodothiophene-2-carboxamide (1.33 g, 0.00314 mol) and 1,1-dimethoxy-N,N-dimethylmethanamine (10.0 mL, 0.0753 mol) was irradiated in the microwave at 120° C. (300 watts) for 30 minutes. The reaction was concentrated in vacuo. The residue dissolved in acetic acid (1.0 mL, 0.18 mol) and hydrazine hydrate (0.69 mL, 0.014 mol) and subjected to microwave irradiation at 120° C. (300 watts) for 15 minutes. The solvent was removed in vacuo and the residue was azeotroped with toluene. Column chromatography was performed to yield the title compound (1.25 g, 85%). LCMS: (FA) ES+, 447. $^1$H NMR (400 MHz, d$_4$-methanol) δ: 8.35 (s, 1H) 7.60 (d, 1H, J=2.0 Hz), 7.45-7.35 (m, 2H).

Step 8: 4-(2,4-dichlorophenyl)-2-(3,6-dihydro-2H-pyran-4-yl)-5-(4H-1,2,4-triazol-3-yl)thiophene-3-carbonitrile A mixture of 4-(2,4-dichlorophenyl)-2-iodo-5-(4H-1,2,4-triazol-3-yl)thiophene-3-carbonitrile (180 mg, 0.4 mmol), tributyl(3,6-dihydro-2H-pyran-4-yl)stannane (0.452 g, 1.2 mmol), lithium chloride (51.2 mg, 1.2 mmol), copper(I) iodide (7.6 mg, 0.04 mmol), tetrakis(triphenylphosphine)palladium (46.4 mg, 0.04 mmol) was dissolved in dioxane (20 mL) and heated to reflux for 3 hours under an atmosphere of argon. The solvent was removed and the residue was purified using ISCO chromatography on silica gel, elution 20% ethyl acetate in hexanes to ethyl acetate to afford the title compound (24 mg, 14%). LCMS: (FA) ES+, 403. $^1$H NMR (400 MHz, d$_4$-methanol) δ: 8.35 (s, 1H), 7.59 (d, 1H), 7.43-7.36 (m, 2H), 6.72 (dd, 1H), 4.38-4.36 (m, 2H), 3.97-3.94 (m, 2H), 2.71-2.68 (m, 2H).

Step 9: 4-(2,4-dichlorophenyl)-2-(tetrahydro-2H-pyran-4-yl)-5-(4H-1,2,4-triazol-3-yl)thiophene-3-carbonitrile 4-(2,4-dichlorophenyl)-2-(3,6-dihydro-2H-pyran-4-yl)-5-(4H-1,2,4-triazol-3-yl)thiophene-3-carbonitrile (20 mg, 0.05 mmol) was dissolved in methanol (2 mL) and 10% Pd/C was added (10 mg). The mixture was stirred under an atmosphere of hydrogen for 2 hours. The suspension was filtered through celite, solvent was evaporated and the residue was purified using ISCO chromatography on silica gel, elution 20% ethyl acetate in hexanes to ethyl acetate to afford the title compound (16 mg, 80%). LCMS: (FA) ES+, 405. $^1$H NMR (400 MHz, d$_4$-methanol) δ: 8.53 (s, 1H), 7.78 (d, 1H), 7.51-7.46 (m, 2H), 4.12-4.08 (m, 1H), 3.99-3.95 (m, 1H), 3.53-3.30 (m, 2H), 3.20-3.15 (m, 1H), 2.00-1.95 (m, 1H), 1.83-1.72 (m, 1H).

EXAMPLE 10

Synthesis of 4-[4-(2,4-dichlorophenyl)-5-(4H-1,2,4-triazol-3-yl)-1,3-thiazol-2-yl]morpholine (Compound I-1)

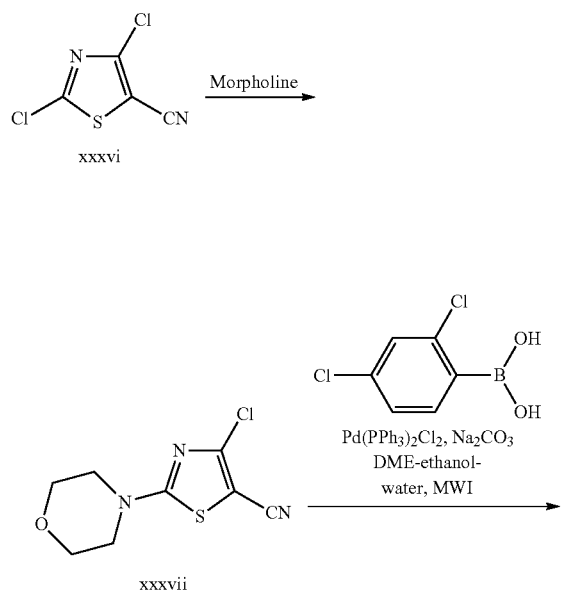

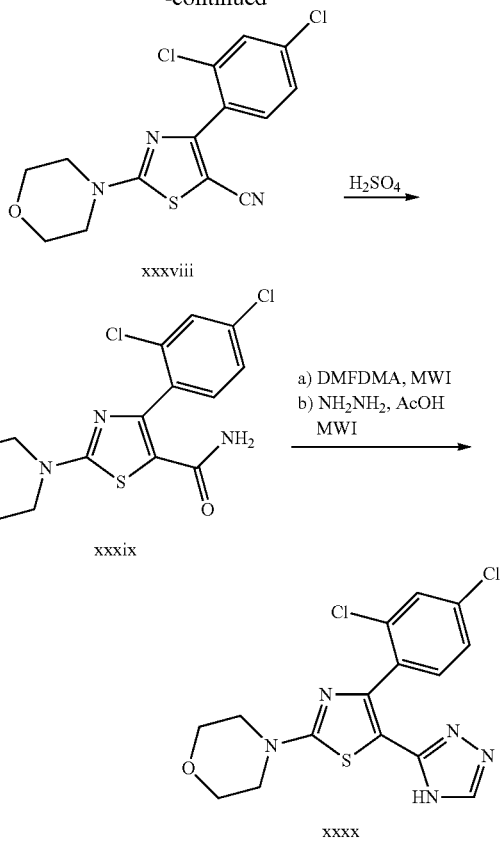

Step 1: Synthesis of 4-chloro-2-morpholin-4-yl-1,3-thiazole-5-carbonitrile 2,4-dichloro-5-cyanothiazole (1.26 g, 0.00704 mol) and N,N-diisopropylethylamine (3.68 mL, 0.0211 mol) were dissolved in ethanol at 70° C. Morpholine (0.614 mL, 0.0704 mol) was added to the hot solution and the mixture was stirred for 30 minutes, cooled down to rt, diluted with water (50 mL) and the formed precipitate was collected to give the title compound (1.55 g, 91%). LCMS: (FA) ES+, 230. $^1$H NMR (300 MHz, d$_6$-DMSO) δ: 3.71-3.67 (m, 4H), 3.52-3.48 (m, 4H).

Step 2: Synthesis of 4-(2,4-dichlorophenyl)-2-morpholin-4-yl-1,3-thiazole-5-carbonitrile 4-chloro-2-morpholin-4-yl-1,3-thiazole-5-carbonitrile (0.200 g, 0.871 mmol), 2,4-dichlorophenylboronic acid (0.249 g, 1.31 mmol), bis(triphenylphosphine)palladium dichloride (0.061 g, 0.0871 mmol), sodium carbonate (0.184 g, 1.74 mmol) were taken up in DME (3 mL), ethanol (1 mL) and water (1 mL) and microwaved at 125° for 30 minutes. Mixture was diluted with ethyl acetate (10 mL) and extracted. The organic phase was dried with sodium sulfate, filtered and evaporated. ISCO purification on silica gel using 10% ethyl acetate in hexane to 50% ethyl acetate in hexane afforded the title compound (45 mg, 15%). LCMS: (FA) ES+, 340. $^1$H NMR (400 MHz, d$_6$-DMSO) δ: 7.44 (d, 1H), 7.20-7.17 (m, 2H), 3.43-3.28 (m, 4H), 3.16-2.93 (m, 4H).

Step 3: Synthesis of 4-(2,4-dichlorophenyl)-2-morpholin-4-yl-1,3-thiazole-5-carboxamide 4-(2,4-dichlorophenyl)-2-morpholin-4-yl-1,3-thiazole-5-carbonitrile (30 mg, 0.088 mmol) was dissolved in sulfuric acid (0.200 mL, 3.75 mmol) and the mixture was stirred at rt for 1 hour. Water (1 mL) was added and the mixture was quenched with an excess of saturated NaHCO₃. Precipitate was filtered off, washed with water and dried to afford the title compound (27 mg, 80%). LCMS: (FA) ES⁺, 358. $^1$H NMR (400 MHz, d$_6$-DMSO) δ: 7.67 (d, 1H), 7.47 (d, 1H), 7.43 (dd, 1H), 3.72-3.69 (m, 4H), 3.44-3.42 (m, 4H).

Step 4: Synthesis of 4-[4-(2,4-dichlorophenyl)-5-(4H-1,2,4-triazol-3-yl)-1,3-thiazol-2-yl]morpholine A mixture of 4-(2,4-dichlorophenyl)-2-morpholin-4-yl-1,3-thiazole-5-carboxamide (23 mg, 0.06 mmol) and 1,1-dimethoxy-N,N-dimethylmethanamine (0.8 mL, 6 mol) was irradiated in the microwave at 160° C. (300 watts) for 30 minutes. The reaction was concentrated in vacuo. The residue dissolved in acetic acid (1.0 mL, 0.18 mol) and hydrazine hydrate (30 mg, 0.7 mmol) and subjected to microwave irradiation at 120° C. (300 watts) for 15 minutes. The solvent was removed in vacuo, the residue was diluted with water (1 mL), the precipitate was collected, washed with water (1 mL) and dried to afford the title compound (10 mg, 40%). LCMS: (FA) ES⁺, 382. $^1$H NMR (400 MHz, d$_6$-DMSO) δ: 13.9 (s, 1H), 8.42 (s, 1H), 7.63 (d, 1H), 7.44-7.42 (m, 2H), 3.73-3.70 (m, 4H), 3.44-3.42 (m, 4H).

II. Biological Data:

Example 1: PI3K Enzyme Assay

Expression and Purification of PI3K Enzyme

Active phosphatidylinositol 3' kinase (PI3K) enzyme was purified at Millennium Pharmaceuticals from SF9 insect cells (Invitrogen) co-infected with baculovirus containing amino-terminal His-tagged p110α and p85α expression constructs.

PI3K Enzyme Homogenous Time Resolved Fluorescence (HTRF®) Assay

The PI3K enzyme HTRF® assay makes use of an energy transfer complex comprised of biotin-PI(3,4,5)P₃, Europhium labeled anti-GST monoclonal antibody, a GST-tagged GRP1 pleckstrin homology (PH) domain, and Streptavidin-APC (allophycocyanin). Excitation of the Europium in the complex results in a stable time-resolved fluorescence resonance energy transfer (FRET) signal. Phosphatidylinositol 3,4,5 triphosphate (PI(3,4,5)P₃, the product of PI3K, disrupts the energy transfer complex by competing with biotin-PI(3,4,5)P₃ for binding to the GRP1 PH domain, resulting in a decreased fluorescent signal. Inhibitors of PI3K in the reaction prevent a decrease in the fluorescent signal.

PI3K enzyme (325 pM) was incubated with di-C8 PI(4,5)P₂ substrate (3.5 μM, CellSignals, Inc.) in assay buffer (50 mM HEPES pH 7.0, 5 mM DTT, 150 mM NaCl, 10 mM β-glycerophosphate, 5 mM MgCl₂, 0.25 mM sodium cholate, 0.001% CHAPS) containing 25 μM ATP and 0.5 μL of test compound (in 100% DMSO) at multiple concentrations in a final volume of 20.5 μL in 384 well plates for 30 min at 22-23° C. The reaction was terminated by adding 5 μL of detection buffer (50 mM HEPES pH7.0, 5 mM DTT, 1 mM NaCl, 10% Tween-20) containing EDTA (90 mM) and biotin-PI(3,4,5)P₃ (150 nM, Echelon Bioscience) to each well. 5 μL of detection buffer containing GST-fused GRP1 PH domain protein (210 nM, Millennium Pharmaceuticals), anti-GST-Europium tagged cryptate antibody (2.25 nM, CisBio), Streptavidin-XL (90 nM, CisBio) and potassium fluoride (240 mM) were then added to each well and incubated for 1 hour. Fluorescent signal for each well was then measured on an LJL_Analyst (Molecular Devices). Concentration response curves were generated by calculating the fluorescent signal in test compound-treated samples relative to DMSO-treated (0% inhibition) and EDTA-treated (100% inhibition) controls, and concentrations producing 50% inhibition (IC$_{50}$ values) were determined from those curves.

Example 2: PI3K Cell Assays

Forkhead Redistribution Assay

Inhibition of PI3K in cells can be assessed using the Forkhead Redistribution Assay (BioImage). Foxo1A fused to EGFP (Foxo1A-EGFP) expressed in U2OS osteosarcoma cells localizes to the cytoplasm when the PI3K pathway is actively signaling. Inactivation of pathway signaling leads to a translocation of the protein from the cytoplasm to the nucleus. Therefore, pathway inhibition can be measured by quantifying the fluorescent intensity of Foxo1A-EGFP within the nucleus.

U2OS cells constitutively expressing Foxo1A-EGFP (6500 cells/well) were plated onto the inner 60 wells of 96 well dishes (BD Falcon OPTILUX black clear bottom) in 100 μL of cell culture media (DMEM (Invitrogen) containing 10% Fetal Bovine Serum (HyClone) and 1% Penicillin-Streptavidin (Invitrogen) and grown overnight in a humidified chamber at 37° C. The cell culture media was removed and the cells were rinsed with 100 μL of low serum media (DMEM containing 0.933% Fetal Bovine Serum and 1% Penicillin-Streptavadin) and incubated in 75 μL of low serum media for 1 hour in a humidified chamber at 37° C. Test compounds (25 μL) at multiple concentrations suspended in DMEM containing 1% Penicillin-Streptavadin were added to cells and incubated in a humidified chamber at 37° C. for 1 hour. The media was removed and the cells were fixed in 100 μL of 4% paraformaldehyde in phosphate buffered saline (PBS) for 10 min and then washed with 100 μL of PBS. DRAQ5 mix (100 μL, Alexis Biochemicals) diluted 1:5000 in PBS containing RNAase (1:10,000, Sigma) was added to cells for 30 minutes. The plates were then imaged (16 fields per well) using an Opera Imager (Evotec) and Foxo1A-EGFP fluorescent intensity within the nucleus (DRAQ5-positive) was quantified using Acapella Software (Evotec). Concentration response curves were generated by calculating the nuclear fluorescent intensity of Foxo-1A EGFP in test compound-treated samples and concentrations producing 50% inhibition (IC$_{50}$ values) relative to the positive control were determined from those curves.

Example 3: Anti-Proliferation Assay

ATPlite Assay

The ATPLite™ (Perkin-Elmer) Assay measures cellular adenosine-triphosphate (ATP) through the generation of a luminescent signal formed from the ATP dependent enzyme firefly luciferase. The luminescent signal intensity can be used as a measure of cellular proliferation, and therefore the anti-proliferative effects of PI3K inhibitors.

Test compounds (4 μL in 100% DMSO) were diluted in 75 μL of Hanks Buffered Saline Solution (Invitrogen). The diluted test compounds (8 μL) were then added to 384-well TC-treated Black/Clear plates (Falcon). HCT-116 cells (American Type Culture Collection) maintained in McCoy's 5a modified media (Invitrogen) containing 10% Fetal Bovine Serum and 1% Penicillin-Streptavadin were added at 1000 cells per well. H460 cells (American Type Culture Collection) maintained in RPMI 1640 containing 10% Fetal Bovine Serum and 1% Penicillin-Streptavadin were added at 1500 cells per well. The cells were then incubated with compound in a humidified chamber at 37° C. for 72 hours. The plates were then removed from the cell culture chambers and allowed to equilibrate to room temperature for 30 min. All but 25 μL of cell culture media was removed from each well, and 25 μl of ATPlite reagent (Perkin Elmer) was added to each well. Luminescence was measured within 5 minutes of adding the ATPlite reagent on a LEADSeeker Luminescence Counter (GE Healthcare Life Sciences). Concentration response curves were generated by calculating the luminescence decrease in test compound-treated samples relative to DMSO-treated controls, and growth inhibition ($IC_{50}$) values were determined from those curves.

As detailed above, compounds of the invention inhibit PI3K. In certain embodiments, compounds of the invention have an IC50<5.0 μM. In other embodiments, compounds of the invention have an IC50<1.0 μM. In still other embodiments, compounds of the invention have an IC50<0.1 μM.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

As detailed above, compounds of the invention inhibit PI3K. In certain embodiments, compounds of the invention have an IC50<5.0 μM. In other embodiments, compounds of the invention have an IC50<1.0 μM. In still other embodiments, compounds of the invention have an IC50<0.1 μM.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:

1. A method of treating a proliferative disorder mediated by PI3K in a patient comprising administering to said patient a therapeutically effective amount of a compound of formula I:

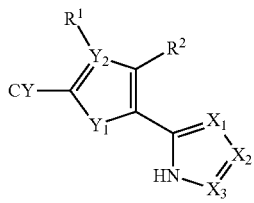

or a pharmaceutically acceptable salt thereof, wherein:
  $Y_1$ is S, O, $NR^8$, wherein $R^8$ is hydrogen or an optionally substituted $C_{1-4}$ aliphatic;
  $Y_2$ is C, N, wherein when $Y_2$ is C, $R^1$ is H, —CN, halogen, —Z—$R^3$, $C_{1-6}$ aliphatic, or 3-10 membered cycloaliphatic, and wherein $Y_2$ is N, $R^1$ is absent; wherein;
  Z is selected from an optionally substituted $C_{1-3}$ alkylene chain, —O—, —N($R^{1a}$)—, —S—, —S(O)—, —S(O)$_2$—, —C(O)—, —CO$_2$—, —C(O)NR$^{1a}$—, —N($R^{1a}$)C(O)—, —N($R^{1a}$)CO$_2$—, —S(O)$_2$NR$^{1a}$—, —N($R^{1a}$)S(O)$_2$—, —OC(O)N($R^{1a}$)—, —N($R^{1a}$)C(O)NR$^{1a}$—, —N($R^{1a}$)S(O)$_2$N($R^{1a}$)—, or —OC(O)—;
  $R^{1a}$ is hydrogen or an optionally substituted $C_{1-4}$ aliphatic, and
  $R^3$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  $R^2$ is H, halogen, —W—$R^5$, or —$R^5$, wherein:
    W is selected from an optionally substituted $C_{1-3}$ alkylene chain, —O—, —N($R^{2a}$)—, —S—, —S(O)—, —S(O)$_2$—, —C(O)—, —CO$_2$—, —C(O)NR$^{2a}$—, —N($R^{2a}$)C(O)—, —N($R^{2a}$)CO$_2$—, —S(O)$_2$NR$^{2a}$—, —N($R^{2a}$)S(O)$_2$—, —OC(O)N($R^{2a}$)—, —N($R^{2a}$)C(O)NR$^{2a}$—, —N($R^{2a}$)S(O)$_2$N($R^{2a}$)—, or —OC(O)—,
    $R^{2a}$ is hydrogen or an optionally substituted $C_{1-4}$ aliphatic, and
    $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  $X_1$, $X_2$, and $X_3$ are each independently N or $CR^6$, wherein each occurrence of $R^6$ is independently hydrogen, —CN, halogen, —V—$R^7$, $C_{1-6}$ aliphatic, or 3-10-membered cycloaliphatic, wherein:
    V is selected from an optionally substituted $C_{1-3}$ alkylene chain, —O—, —N($R^{6a}$)—, —S—, —S(O)—, —S(O)$_2$—, —C(O)—, —CO$_2$—, —C(O)NR$^{6a}$—, —N($R^{6a}$)C(O)—, —N($R^{6a}$)CO$_2$—, —S(O)NR$^{6a}$—, —N($R^{6a}$)S(O)$_2$—, —OC(O)N($R^{6a}$)—, —N($R^{6a}$)C(O)NR$^{6a}$—, —N($R^{6a}$)S(O)$_2$N($R^{6a}$)—, or —OC(O)—,
    $R^{6a}$ is hydrogen or an optionally substituted $C_{1-4}$ aliphatic, and
    $R^7$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  CY is

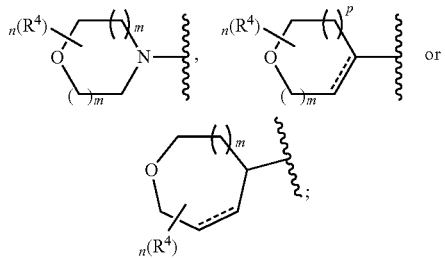

wherein each occurrence of $R^4$ is independently —$R^{4a}$ or -$T_1$—$R^{4d}$, wherein:
  each occurrence of $R^{4a}$, as valency and stability permit, is independently fluorine, =O, =S, —CN, —NO$_2$, —$R^{4c}$, —N($R^{4b}$)$_2$, —O$R^{4b}$, —S$R^{4c}$, —S(O)$_2R^{4C}$, —C(O)$R^{4b}$, —C(O)O$R^{4b}$, C(O)N($R^{4b}$)$_2$, —S(O)$_2$N($R^{4b}$)$_2$, —OC(O)N($R^{4b}$)$_2$, —N($R^{4e}$)C(O)$R^{4b}$, —N($R^{4e}$)SO$_2R^{4c}$, N($R^{4e}$)C(O)O$R^{4b}$, —N($R^{4e}$)C(O)N($R^{4b}$)$_2$, or —N($R^{4e}$)SO$_2$N($R^{4b}$)$_2$, or two occurrences of $R^{4b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{4b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4e}$ is independently hydrogen or an optionally substituted $C_{1-6}$ aliphatic group; and $T_1$ is an optionally substituted $C_1$-$C_6$ alkylene chain wherein the alkylene chain optionally is interrupted by —N($R^{4a}$)—, —O—, —S—, —S(O)—, —S(O)$_2$—, —C(O)—, —C(O)O—, —C(O)N($R^{4a}$)—, —S(O)$_2$N($R^{4a}$)—, —OC(O)N($R^{4a}$)—, —N($R^{4a}$)C(O)—, —N($R^{4a}$)SO$_2$—, —N($R^{4a}$)C(O)O—, —NR$^{4a}$C(O)N($R^{4a}$)—, —N($R^{4a}$)S(O)$_2$N($R^{4a}$)—, —OC(O)—, or —C(O)N($R^{4a}$)—O— or wherein $T_1$ or a portion thereof optionally forms part of an optionally substituted 3-7 membered cycloaliphatic or heterocyclyl ring;

n is 0-6;
m is 1 or 2;
p is 0, 1, or 2; and
===== represents a single or double bond.

2. The method of claim 1, wherein the proliferative disorder is breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

3. A method of treating an inflammatory or cardiovascular disorder mediated by PI3K in a patient comprising administering to said patient a therapeutically effective amount of a compound of formula I:

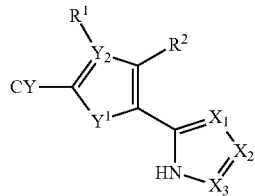

or a pharmaceutically acceptable salt thereof, wherein:
$Y_1$ is S, O, NR$^8$, wherein R$^8$ is hydrogen or an optionally substituted $C_{1-4}$ aliphatic;

$Y_2$ is C, N, wherein when $Y_2$ is C, $R^1$ is H, —CN, halogen, —Z—R$^3$, $C_{1-6}$ aliphatic, or 3-10 membered cycloaliphatic, and wherein $Y_2$ is N, $R^1$ is absent; wherein;

Z is selected from an optionally substituted $C_{1-3}$ alkylene chain, —O—, —N(R$^{1a}$)—, —S—, —S(O)—, —S(O)$_2$—, —C(O)—, —CO$_2$—, —C(O)NR$^{1a}$—, —N(R$^{1a}$)C(O)—, —N(R$^{1a}$)CO$_2$—, —S(O)$_2$NR$^{1a}$—, —N(R$^{1a}$)S(O)$_2$—, —OC(O)N(R$^{1a}$)—, —N(R$^{1a}$)C(O)NR$^{1a}$—, —N(R$^{1a}$)S(O)$_2$N(R$^{1a}$)—, or —OC(O)—;

R$^{1a}$ is hydrogen or an optionally substituted $C_{1-4}$ aliphatic, and

R$^3$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

R$^2$ is H, halogen, —W—R$^5$, or —R$^5$, wherein:
W is selected from an optionally substituted $C_{1-3}$ alkylene chain, —O—, —N(R$^{2a}$)—, —S—, —S(O)—, —S(O)$_2$—, —C(O)—, —CO$_2$—, —C(O)NR$^{2a}$—, —N(R$^{2a}$)C(O)—, —N(R$^{2a}$)CO$_2$—, —S(O)$_2$NR$^{2a}$—, —N(R$^{2a}$)S(O)$_2$—, —OC(O)N(R$^{2a}$)—, —N(R$^{2a}$)C(O)NR$^{2a}$—, —N(R$^{2a}$)S(O)$_2$N(R$^{2a}$)—, or —OC(O)—, R$^{2a}$ is hydrogen or an optionally substituted $C_{1-4}$ aliphatic, and R$^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$X_1$, $X_2$, and $X_3$ are each independently N or CR$^6$, wherein each occurrence of R$^6$ is independently hydrogen, —CN, halogen, —V—R$^7$, $C_{1-6}$ aliphatic, or 3-10-membered cycloaliphatic, wherein:
V is selected from an optionally substituted $C_{1-3}$ alkylene chain, —O—, —N(R$^{6a}$)—, —S—, —S(O)—, —S(O)$_2$—, —C(O)—, —CO$_2$—, —C(O)NR$^{6a}$—, —N(R$^{6a}$)C(O)—, —N(R$^{6a}$)CO$_2$—, —S(O)$_2$NR$^{6a}$—, —N(R$^{6a}$)S(O)$_2$—, —OC(O)N(R$^{6a}$)—, —N(R$^{6a}$)C(O)NR$^{6a}$—, —N(R$^{6a}$)S(O)$_2$N(R$^{6a}$)—, or —OC(O)—, R$^{6a}$ is hydrogen or an optionally substituted $C_{1-4}$ aliphatic, and R$^7$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

CY is

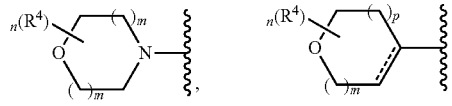

-continued or 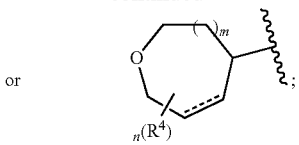

wherein each occurrence of $R^4$ is independently —$R^{4a}$ or -$T_1$—$R^{4d}$, wherein:
  each occurrence of $R^{4a}$, as valency and stability permit, is independently fluorine, =O, =S, —CN, —$NO_2$, —$R^{4c}$, —$N(R^{4b})_2$, —$OR^{4b}$, —$SR^{4c}$, —$S(O)_2R^{4c}$, —$C(O)R^{4b}$, —$C(O)OR^{4b}$, $C(O)N(R^{4b})_2$, —$S(O)_2N(R^{4b})_2$, —$OC(O)N(R^{4b})_2$, —$N(R^{4e})C(O)R^{4b}$, —$N(R^{4e})SO_2R^{4c}$, $N(R^{4e})C(O)OR^{4b}$, —$N(R^{4e})C(O)N(R^{4b})_2$, or —$N(R^{4e})SO_2N(R^{4b})_2$, or two occurrences of $R^{4b}$, taken together with a nitrogen atom to which they are bound, form an optionally substituted 4-7-membered heterocyclyl ring having 0-1 additional heteroatoms selected from nitrogen, oxygen, or sulfur;
  each occurrence of $R^{4b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{4c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{4d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{4e}$ is independently hydrogen or an optionally substituted $C_{1-6}$ aliphatic group; and
  $T_1$ is an optionally substituted $C_1$-$C_6$ alkylene chain wherein the alkylene chain optionally is interrupted by —$N(R^{4a})$—, —O—, —S—, —$S(O)$—, —$S(O)_2$—, —$C(O)$—, —$C(O)O$—, —$C(O)N(R^{4a})$—, —$S(O)_2N(R^{4a})$—, —$OC(O)N(R^{4a})$—, —$N(R^{4a})C(O)$—, —$N(R^{4a})SO_2$—, —$N(R^{4a})C(O)O$—, —$NR^{4a}C(O)N(R^{4a})$—, —$N(R^{4a})S(O)_2N(R^{4a})$—, —$OC(O)$—, or —$C(O)N(R^{4a})$—O— or wherein $T_1$ or a portion thereof optionally forms part of an optionally substituted 3-7 membered cycloaliphatic or heterocyclyl ring;
n is 0-6;
m is 1 or 2;
p is 0, 1, or 2; and
===== represents a single or double bond.

4. The method of claim 3, wherein the inflammatory or cardiovascular disorder is selected from allergies/anaphylaxis, acute and chronic inflammation, rheumatoid arthritis; autoimmunity disorders, thrombosis, hypertension, cardiac hypertrophy, and heart failure.

5. A method for inhibiting PI3K activity in a patient comprising administering a composition comprising an amount of a compound of formula I:

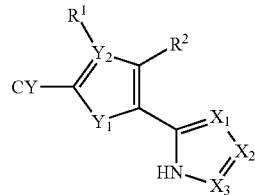

or a pharmaceutically acceptable salt thereof, wherein:
  $Y_1$ is S, O, $NR^8$, wherein $R^8$ is hydrogen or an optionally substituted $C_{1-4}$aliphatic;
  $Y_2$ is C, N, wherein when $Y_2$ is C, $R^1$ is H, —CN, halogen —Z—$R^3$, $C_{1-6}$ aliphatic or 3-10 membered cycloaliphatic and wherein $Y_2$ is N, $R^1$ is absent; wherein;
  Z is selected from an optionally substituted $C_{1-3}$ alkylene chain, —O—, —$N(R^{1a})$—, —S—, —$S(O)$—, —$S(O)_2$—, —$C(O)$—, —$CO_2$—, —$C(O)NR^{1a}$—, —$N(R^{1a})C(O)$—, —$N(R^{1a})CO_2$—, —$S(O)_2NR^{1a}$—, —$N(R^{1a})S(O)_2$—, —$OC(O)N(R^{1a})$—, —$N(R^{1a})C(O)NR^{1a}$—, —$N(R^{1a})S(O)_2N(R^{1a})$—, or —$OC(O)$—;
  $R^{1a}$ is hydrogen or an optionally substituted $C_{1-4}$ aliphatic, and
  $R^3$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  $R^2$ is H, halogen, —W—$R^5$, or —$R^5$, wherein:
  W is selected from an optionally substituted $C_{1-3}$ alkylene chain, —O—, —$N(R^{2a})$—, —S—, —$S(O)$—, —$S(O)_2$—, —$C(O)$—, —$CO_2$—, —$C(O)NR^{2a}$—, —$N(R^{2a})C(O)$—, —$N(R^{2a})CO_2$—, —$S(O)_2NR^{2a}$—, —$N(R^{2a})S(O)_2$—, —$OC(O)N(R^{2a})$—, —$N(R^{2a})C(O)NR^{2a}$—, —$N(R^{2a})S(O)_2N(R^{2a})$—, or —$OC(O)$—,
  $R^{2a}$ is hydrogen or an optionally substituted $C_{1-4}$ aliphatic, and
  $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  $X_1$, $X_2$, and $X_3$ are each independently N or $CR^6$, wherein each occurrence of $R^6$ is independently hydrogen, —CN, halogen, —V—$R^7$, $C_{1-6}$ aliphatic, or 3-10-membered cycloaliphatic, wherein:
  V is selected from an optionally substituted $C_{1-3}$ alkylene chain, —O—, —$N(R^{6a})$—, —S—, —$S(O)$—, —$S(O)_2$—, —$C(O)$—, —$CO_2$—, —$C(O)NR^{6a}$—, —$N(R^{6a})C(O)$—, —$N(R^{6a})CO_2$—, —$S(O)_2NR^{6a}$—, —$N(R^{6a})S(O)_2$—, —$OC(O)N(R^{6a})$—, —$N(R^{6a})C(O)NR^{6a}$—, —$N(R^{6a})S(O)_2N(R^{6a})$—, or —$OC(O)$—,
  $R^{6a}$ is hydrogen or an optionally substituted $C_{1-4}$ aliphatic, and $R^7$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

CY is

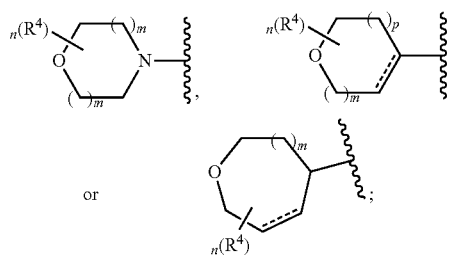

wherein each occurrence of $R^4$ is independently $—R^{4a}$ or $-T_1—R^{4d}$, wherein:

each occurrence of $R^{4a}$, as valency and stability permit, is independently fluorine, =O, =S, —CN, —NO$_2$, —$R^{4c}$, —N($R^{4b}$)$_2$, —O$R^{4b}$, —S$R^{4c}$, —S(O)$_2R^{4c}$, —C(O)$R^{4b}$, —C(O)O$R^{4b}$, C(O)N($R^{4b}$)$_2$, —S(O)$_2$N($R^{4b}$)$_2$, —OC(O)N($R^{4b}$)$_2$, —N($R^{4e}$)C(O)$R^{4b}$, —N($R^{4e}$)SO$_2R^{4c}$, N($R^{4e}$)C(O)O$R^{4b}$, —N($R^{4e}$)C(O)N($R^{4b}$)$_2$, or —N($R^{4e}$)SO$_2$N($R^{4b}$)$_2$, or two occurrences of $R^{4b}$, taken together with a nitrogen atom to which they are bound, form an optionally substituted 4-7-membered heterocyclyl ring having 0-1 additional heteroatoms selected from nitrogen, oxygen, or sulfur;

each occurrence of $R^{4b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4d}$ is independently hydrogen or an optionally substituted from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{4e}$ is independently hydrogen or an optionally substituted $C_{1-6}$ aliphatic group; and $T_1$ is an optionally substituted $C_1$-$C_6$ alkylene chain wherein the alkylene chain optionally is interrupted by —N($R^{4a}$)—, —O—, —S—, —S(O)—, —S(O)$_2$—, —C(O)—, —C(O)O—, —C(O)N($R^{4a}$)—, —S(O)$_2$N($R^{4a}$)—, —OC(O)N($R^{4a}$)—, —N($R^{4a}$)C(O)—, —N($R^{4a}$)SO$_2$—, —N($R^{4a}$)C(O)O—, —N$R^{4a}$C(O)N($R^{4a}$)—, —N($R^{4a}$)S(O)$_2$N($R^{4a}$)—, —OC(O)—, or —C(O)N($R^{4a}$)—O— or wherein $T_1$ or a portion thereof optionally forms part of an optionally substituted 3-7 membered cycloaliphatic or heterocyclyl ring;

n is 0-6;

m is 1 or 2;

p is 0, 1, or 2; and

===== represents a single or double bond effective to inhibit PI3K activity in the patient.

* * * * *